(12) United States Patent
Ackermann et al.

(10) Patent No.: US 7,897,156 B2
(45) Date of Patent: Mar. 1, 2011

(54) MODIFIED VACCINIA VIRUS ANKARA FOR THE VACCINATION OF NEONATES

(75) Inventors: Mathias Ackermann, Basserdorf (CH); Mark Suter, Lucerne (CH); Hans Peter Hefti, Zurich (CH); Ruth Hefti, legal representative, Zurich (CH); Marco Franchini, Suhr (CH); Sabine Vollstedt, Bokhold-Hanredder (DE); Paul Chaplin, Munich (DE)

(73) Assignee: Bavarian Nordic A/S, Kvistgaard (DK)

( * ) Notice: Subject to any disclaimer, the term of this patent is extended or adjusted under 35 U.S.C. 154(b) by 158 days.

(21) Appl. No.: 12/118,841

(22) Filed: May 12, 2008

(65) Prior Publication Data

US 2009/0104224 A1 Apr. 23, 2009

Related U.S. Application Data

(63) Continuation-in-part of application No. 11/341,955, filed on Jan. 27, 2006, now abandoned, which is a continuation-in-part of application No. 10/418,854, filed on Apr. 18, 2003, now Pat. No. 7,097,842, which is a continuation-in-part of application No. PCT/EP01/13628, filed on Nov. 11, 2001.

(30) Foreign Application Priority Data

Apr. 19, 2002 (DK) .............................. 2002 00590

(51) Int. Cl.
*A61K 31/285* (2006.01)
(52) U.S. Cl. ................................. 424/232.1; 424/281.1
(58) Field of Classification Search ........................ None
See application file for complete search history.

(56) References Cited

U.S. PATENT DOCUMENTS

| | | | |
|---|---|---|---|
| 3,914,408 A | 10/1975 | Mebus | |
| 4,191,745 A | 3/1980 | Mayr et al. | |
| 5,338,683 A | 8/1994 | Paoletti | |
| 5,403,582 A | 4/1995 | Nazerian et al. | |
| 5,405,772 A | 4/1995 | Ponting | |
| 5,753,489 A | 5/1998 | Kistner et al. | |
| 5,756,341 A | 5/1998 | Kistner et al. | |
| 5,770,212 A | 6/1998 | Falkner et al. | |
| 5,843,456 A | 12/1998 | Paoletti et al. | |
| 6,190,655 B1 | 2/2001 | Lyman et al. | |
| 6,204,250 B1 | 3/2001 | Bot et al. | |
| 6,605,465 B1 | 8/2003 | Paoletti | |
| 6,685,950 B2 | 2/2004 | Weber et al. | |
| 6,761,893 B2 * | 7/2004 | Chaplin et al. | ........... 424/199.1 |
| 6,805,870 B1 | 10/2004 | Mayr | |
| 6,913,752 B2 | 7/2005 | Chaplin et al. | |
| 7,097,842 B2 | 8/2006 | Suter et al. | |
| 7,189,536 B2 * | 3/2007 | Chaplin et al. | ............. 435/69.1 |
| 7,335,364 B2 | 2/2008 | Chaplin et al. | |
| 7,338,662 B2 * | 3/2008 | Howley et al. | ........... 424/232.1 |
| 7,384,644 B2 * | 6/2008 | Chaplin et al. | ........... 424/232.1 |
| 7,445,924 B2 * | 11/2008 | Chaplin et al. | .............. 435/239 |
| 7,618,980 B2 | 11/2009 | Fevig et al. | |
| 7,628,980 B2 | 12/2009 | Suter et al. | |
| 2003/0215466 A1 * | 11/2003 | Chaplin et al. | ........... 424/232.1 |
| 2004/0091995 A1 * | 5/2004 | Schlom et al. | ........... 435/235.1 |
| 2005/0214323 A1 | 9/2005 | Chaplin et al. | |
| 2006/0127984 A1 | 6/2006 | Ackermann et al. | |
| 2006/0280758 A1 | 12/2006 | Chaplin et al. | |
| 2008/0089907 A1 | 4/2008 | Chaplin et al. | |
| 2009/0169579 A1 | 7/2009 | Chaplin et al. | |
| 2010/0119545 A1 | 5/2010 | Chaplin et al. | |

FOREIGN PATENT DOCUMENTS

| | | |
|---|---|---|
| EP | 1335987 B1 | 12/2005 |
| GB | 2370573 A1 | 7/2002 |
| WO | 90/12882 A1 | 11/1990 |
| WO | 95/22978 A1 | 8/1995 |
| WO | 97/02355 A1 | 1/1997 |
| WO | 97/31119 A1 | 8/1997 |
| WO | 98/13500 A2 | 4/1998 |
| WO | 98/17283 A1 | 4/1998 |
| WO | 98/56919 A2 | 12/1998 |
| WO | 99/07869 A1 | 2/1999 |
| WO | 00/29428 A1 | 5/2000 |
| WO | 01/68820 A1 | 9/2001 |

(Continued)

OTHER PUBLICATIONS

Mayr et al (Developments in Biological Standardization 41:255-234, 1978).*
Vollstedt et a., Flt3 Ligand-treated Neonatal Mice Have Increased Innate Immuity Against Intracellular Pathogens and Efficiently Control Virus Infections, J. Exp. Med. 197:575-584 (2003).
Franchini et al., Dendritic Cells from Mice Neonatally Vaccinated with Modified Vaccinia Virus Ankara Transfer Resistance against Herpes Simplex Virus Type I to Naive One-Week-Old Mice1, J. Immunology 172: 6304-6312 (2004).
Sutter et al., Nonreplicating vaccinia vector efficiently expresses recombinant genes. P.N.A.S. 89:10847-10851, 1992.
Blanchard et al., Modified vaccinia virus Ankara undergoes limited replication in human cells and lacks several immunomodulatory proteins: implications for use as a human vaccine. J. Gen Virology 79:1159-1167, 1998.

(Continued)

*Primary Examiner* — Mary E Mosher
(74) *Attorney, Agent, or Firm* — Law Office of Salvatore Arrigo

(57) ABSTRACT

The invention concerns the use of a virus to increase the number of dendritic cells or their precursor cells in an immunocompromised animal, including a human. The virus is preferably a Modified Vaccinia Virus Ankara which is capable of infecting the cells of a neonatal or prenatal animal, including a human, but not capable of being replicated to infectious progeny virus in the neonatal or prenatal animal, including a human.

12 Claims, 8 Drawing Sheets

FOREIGN PATENT DOCUMENTS

Figure 1A:
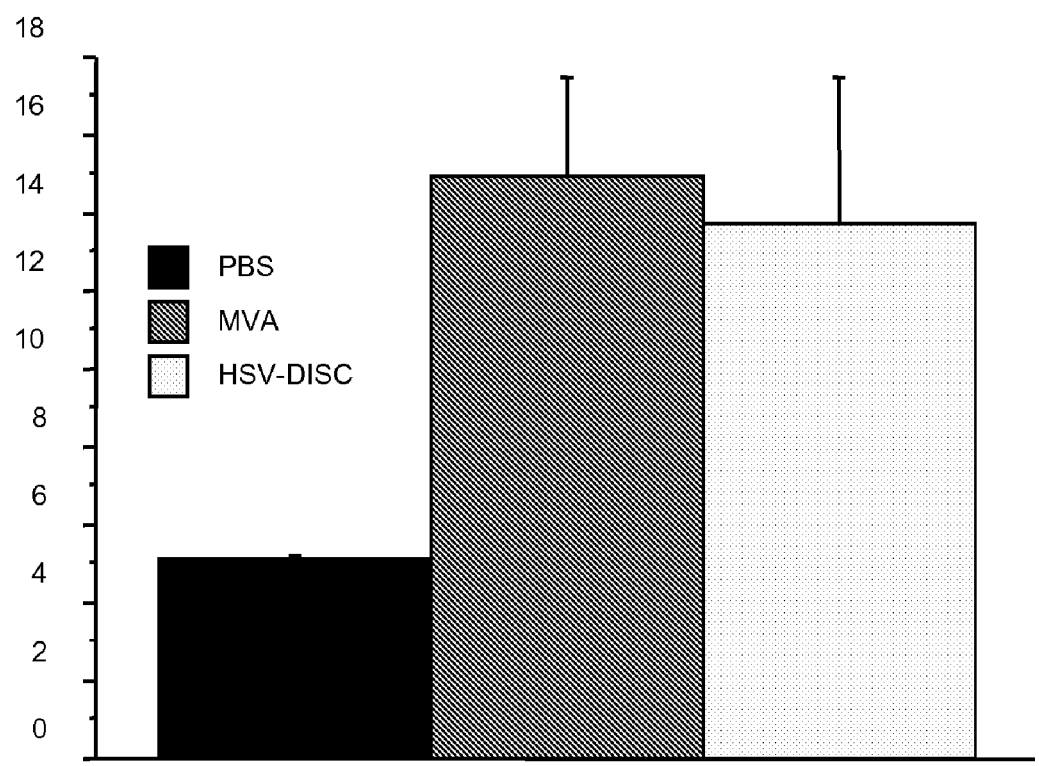

| WO | 01/95919 A2 | 12/2001 |
|---|---|---|
| WO | 02/42480 A2 | 5/2002 |
| WO | WO 2005/046614 * | 5/2005 |

OTHER PUBLICATIONS

Schiver et al., Replication-incomptent adenoviral vaccine vector elicits effective anti-immunodeficiency-virus immunity. Nature 415:331-335, 2002.

Drexler et al., Modified Vaccinia Virus Ankara for Delivery of Human Tyrosinase as Melanmaasociated Antigen: Induction of Tyrosinase- and Melanoma-specific Human Leukocyte Antigen A*0201-restricted Cytotoxic T Cells in Vitro and in Vivo. Cancer Research 59:4955-5963, 1993.

Oxford Biomedica PLC et al., Defendants' Answer to Plaintiff's First Amended Complaint and Counterclaims, Case No. 08cv1156-MMA (RBB), Jun. 1, 2009.

Bavarian Nordic A/S, Plaintiffs Answers to Defendants' Counterclaims, Case No. 08cv1156- MMA (RBB), Jun. 22, 2009.

Bavarian Nordic A/S, Plaintiffs Motion for Partial Summary Judgement on Inequitable Conduct, Case No. 08cv1156-MMA (RBB), Jan. 25, 2010.

Declaration of Theodore J. Folkman, Case No. 08cv1156-MMA (RBB), Jan. 25, 2010.

Suter et al., Modified vaccinia Ankara strains with identical coding sequences actually represent complex mixtures of viruses that determine the biological properties of each strain, Vaccine 27:7442-7450 (2009).

Opposition Division, EPO, Opposition to EP Patent No. 1420822, EPA Form 2906, Oct. 8, 2009.

Emergent Product Development Germany GMBH, Opposition to EP Patent No. 1420822, Reply Letter, Sep. 23, 2009.

Bavarian Nordic, Opposition to EP Patent No. 1420822, Patentee Response to Oppositions, Mar. 27, 2009.

Sanofi Pasteur, Opposition to EP Patent No. 1420822, Notice of Opposition, Apr. 11, 2008.

Emergent Product Development Germany GMBH, Opposition to EP Patent No. 1420822, Notice of Opposition, Apr. 8, 2008.

Dr. Elfriede Dworak of the Commertcial Court of Vienna, Austria, Decision on Initial Matter, without prejudice, in Case 19Cg 25/06g, May 31, 2007.

Mayr & Mayr, Pesq. Vet. Bras. 19:91-98 (1999).

Mayr et al., Infection 3:6-14 (1975).

Mayr et al., J. Vet Med. B. 3681-99 (1989).

Mayr et al., Drug Res. 37:988-989 (1987).

Mayr et al., J. Vet Med. B. 33:321-339 (1986).

Dr. Paul Chaplin, ITC Testimony, ITC Investigation No. 337-TA-550, 447-706, May 10, 2006.

Mayr, Swiss Vet.11:13-17 (1999).

Paul Luckern, ALJ, Order No. 5, ITC Investigation No. 337-TA-550, Jun. 29, 2007.

Bavarian Nordic, 1999 Annual Report, Mar. 14, 2000.

Bavarian Nordic, 2000 Annual Report, Mar. 6, 2001.

Oxford Biomedica (UK) LTD, Opposition to EP Patent No. 1335987, Additional Submissions, Dec. 7, 2009.

Bavarian Nordic, Opposition to EP Patent No. 1335987, Reply to Submissions, Jun. 18, 2008.

Oxford Biomedica (UK) LTD, Opposition to EP Patent No. 1335987, Reply to Patentee's Response, Jan. 28, 2008.

Emergent Product Development Germany GMBH, Opposition to EP Patent No. 1335987, Submission to Patentee's Observations, Mar. 12, 2008.

Bavarian Nordic, Opposition to EP Patent No. 1335987, Response to Oppositions, Aug. 1, 2007.

Emergent Product Development Germany GMBH, Opposition to EP Patent No. 1335987, Notice of Opposition, Sep. 28, 2006.

VIRBAC SA, Opposition to EP Patent No. 1335987, Notice of Opposition, Sep. 28, 2006.

Innogenetics NV, Opposition to EP Patent No. 1335987, Notice of Opposition, Sep. 27, 2006.

Oxford Biomedica (UK) LTD, Opposition to EP Patent No. 1335987, Notice of Opposition, Sep. 26, 2006.

Baxter Ag, Opposition to EP Patent No. 1335987, Notice of Opposition, May 15, 2006.

Sanofi Pasteur Inc, Opposition to EP Patent No. 1335987, Notice of Opposition, Sep. 26, 2006.

Acambis PLC, Opposition to EP Patent No. 1335987, Notice of Opposition, May 15, 2006.

Drexler et al., Highly attenuated modified vaccinia virus Ankara replicates in baby hamster kidney cells, a potential host ofr virus propagation, but not in various human transformed and primary cells, Journal of General Virology (1998), 79, 347-352.

Drexler, et al., J. Gen. Virol. (1998) 79:347-352.

International Preliminary Examination Report, dated Jan. 11, 2006, four (4) pages.

Tartaglia, et al. "NYVAC: a highly attenuated strain of vaccinia virus"—Virology 1992, vol. 188, pp. 217-232.

Kovarik, et al. "Induction of adult-like antibody, Th1, and CTL responses to measles hemagglutinin by early life murine immunization with an attenuated vaccinia-derived NYVAC (K1L) viral vector" Virology Jun. 20, 2001, vol. 285, pp. 12-20.

Kazanji. et al. "Immunogenicity and protective efficacy of recombinant human T-cell leukaemia/lymphoma virus type 1 NYVAC and naked DNA vaccine candidates in squirrel monkeys (Saimiri sciureus)" Journal of Virology, Jul. 2001, vol. 75(13), pp. 5939-5948.

U.S. International Trade Commission, Inv. No. 337-Ta-550, Order No. 10: Denying Respondent's Motion to Terminate and Entry of Consent Order, Nov. 30, 2005, pp. 1-8.

Inv. No. 337-TA-550, Complainant Bavarian Nordic's Motion for Summary Determination of Infringement of the '893 Patent, Mar. 20, 2005, pp. 1-15.

U.S. International Trade Commission, Inv. No. 337-TA-550, Complainant's Petition for Review of the Final Initial Determination, Sep. 18, 2006, pp. 1-52.

U.S. International Trade Commission, Inv. No. 337-TA-550, Order No. 16: Granting Complainant's Motion to Declassify Confidential Information, Feb. 15, 2006, pp. 1-8.

U.S. International Trade Commission, Inv. No. 337-TA-550, Bavarian Nordic's Complaint Under Section 337 of the Tariff Act of 1930, Aug. 19, 2005, pp. 1-30.

Federal Register, vol. 70, No. 184, Sep. 23, 2005, pp. 55918-55919.

U.S. International Trade Commission, Inv. No. 337-TA-550, Memorandum in Opposition to Respondent's Motion to Terminate, Nov. 28, 2005, pp. 1-17.

U.S. International Trade Commission, Inv. No. 337-TA-550, Memorandum in Support of Respondent's Motion for Summary Determination, Mar. 30, 2005, pp. 1-48.

U.S. International Trade Commission, Inv. No. 337-TA.:550, Appendix to Memorandum in Support of Respondent's Motion for Summary Determination, vol. 1 of 3, Oct. 31, 2005, pp. 1-64.

U.S. International Trade Commission, Inv. No. 337-TA-550, Appendix to Memorandum in Support of Respondent's Motion for Summary Determination, vol. 2 of 3, Dec. 1, 2005, pp. 1-45.

U.S. International Trade Commission, Inv. No. 337-TA-550, Appendix to Memorandum in Support of Respondent's Motion for Summary Determination, vol. 3 of 3.

U.S. International Trade Commission, Inv. No. 337-TA-550, Supplemental Appendix.

U.S. International Trade Commission, Inv. No. 337-TA-550, Notice of Investigation, Sep. 19, 2005.

U.S. International Trade Commission, Inv. No. 337-TA-550, Respondent's Opposition to Complainant's Motion to Declassify Confidential Information, Feb. 13, 2006, pp. 1-9.

U.S. International Trade Commission, Inv. No. 337-TA-550, Motion for Leave to File Reply in Support of Respondent's Motion for Summary Determination (pp. 1-2), Respondent's Certification Pursuant to Ground Rule 3.2 (p. 1), and Reply in Support of Respondent's Motion for Summary Determination, Apr. 5, 2005 (pp. 1-3), Apr. 5, 2006.

U.S. International Trade Commission, Inv. No. 337-TA-550, Respondent's Notice of Prior Art, Feb. 3, 2006, pp. 1-8.

U.S. International Trade Commission, Inv. No. 337-TA-550, Response of Acambis plc Under Section 337 of the Tariff Act of 1930 and Notice of Investigation, Oct. 21, 2005, pp. 1-24.

U.S. International Trade Commission, Inv. No. 337-TA-550, Commission Investigative Staffs Response to the Private Parties' Motions in Limine, May 3, 2006, pp. 1-5.

U.S. International Trade Commission, Inv. No. 337-TA-550, Commission Investigative Staffs Notice of Prior Art, Feb. 3, 2006.

U.S. International Trade Commission, Inv. No. 337-TA-550, Consent Order Stipulation, Nov. 2, 2005, pp. 1-4.

U.S. International Trade Commission, Inv. No. 337-TA-550, Consent Order Stipulation (pp. 1-4) with Commission Opinion of Feb. 21, 2007pp. 1-39.

U.S. International Trade Commission, Inv. No. 337-TA-550, Office of Unfair Import Investigation's Response to Commission Notice of Jan. 19, 2007 Jan. 26, 2007, pp. 1-8.

U.S. International Trade Commission, Inv. No. 337-TA-550, Office of Unfair Import Investigations' Combined Response to Bavarian Nordic and Acambis PLC's Responses to Questions Posed by the Commission, Dec. 22, 2006, pp. 1-23.

U.S. International Trade Commission, Inv. No. 337-TA-550, Office of Unfair Import Investigations' Response to Questions Posed in the Commission's Order of Nov. 22, 2006 and Briefing on the Issues of Remedy, Public Interest, and Bonding, Dec. 12 2006, 1-30.

Inv. No. 337-TA-550, Ofifce of Unfair Import Investigations' Response to Petitions for Review, pp. 1-33.

U.S. International Trade Commission, Inv. No. 337-TA-550, Office of Unfair Import Investigations' Petition for Review.

U.S. International Trade Commission, Inv. No. 337-TA-550, Initial Determination on Violation of Section 337 and Recommended Determination on Remedy and Bonding, Sep. 6, 2006.

U.S. International Trade Commission, Inv. No. 337-TA-550, Respondent's Post-Hearing Brief, Aug. 15, 2006, pp. 1-80.

U.S. International Trade Commission, Inv. No. 337-TA-550, Complainant's Response to Respondent's Petition for Commission Review of the Initial Determination, Sep. 25, 2006, pp. 1-20.

U.S. International Trade Commission, Inv. No. 337-TA-550, Complainant's Response to the Ouii Petition for Commission Review of the Initial Determination, Sep. 25, 2006, pp. 1-11.

U.S. International Trade Commission, Inv. No. 337-TA-550, Complainant Bavarian Nordic's Opening Written Submission to the Commission on the Issues Under Review Associated with the Final Initial Determination and Order No. 10, Jan. 2412007, pp. 1-72.

U.S. International Trade Commission, Inv. No. 337-TA-550, Complainant Bavarian Nordic's Response to OUII's Response to Questions Posed in the Commission's Order of Nov. 22, 2006 and Briefing on the Issues of Remedy, Public Interest, and Bonding, Jan. 18, 2007, pp. 1-12.

U.S. International Trade Commission, Inv. No. 337-TA-550, Complainant Bavarian Nordic's Opening Written Submission to the Commission on the Issues Under Review Associated with the Final Initial Determination and Order No. 10, Jan. 24, 2007, pp. 1-72.

U.S. International Trade Commission, Inv. No. 337-TA-550, Notice of Commission Decision to Review the Final Initial Determination; Extension of the Target Date for Completion of the Investigation; Schedule for Briefing on the Issues on Review and Remedy, Public Interest, and Bonding, November 22, 20061pp. 1-6.

Du et al., PNAS 93:9693-9698, 1996.

Oh et al., Journal of Virology 79:12852-12860, 2005.

Hirsch et al., Patterns of Viral Replication Correlate with Outcome in Simian Immunodeficiency Virus (SIV)-Infected Macaques: Effect of Prior Immunization with a Trivalent SIV Vaccine in Modified Vaccinia Virus Ankara, J. Virol. 70:3741-3752, 1996.

Zhu et al., Evaluation of Recombinant Vaccinia Virus—Measles Vaccines in Rhesus Macaques with Preexisting Measles Antibody, Virology 276:202-213, 2000.

Roberts, Drug Discovery Today 7:936-937, 2002.

Kovarik et al., Induction of Adult-like Antibody, Th1, and CTL Responses to Measles Hemagglutinin by Early Life Murine Immunization with an Attenuated Vaccinia-Derived NYVAC (KIL) Viral Vector, Virology 285:12-20, 2001.

Dadaglio et al., Efficient in Vivo Priming of Specific Cytotoxic T Cell Responses by Neonatal Dendritic Cells, J. Immmunology 168:2219-2224, 2002.

Ridge et al., Neonatal Tolerance Revisited: Turning on Newborn T Cells with Dendritic Cells, Science 271:1723-1726, 1996.

B. Vilsmeier, Paraimmunity inducing effects of vaccinia strain MVA. (1999) Bed. Munch. Tierarztl. Wschr. 112:329-333.

A. Mayr. Paraspeziifsche Vaccinen aus Pockenviren (Paramunitatsinducer): eine neue Art von Impfstoff (1999) Azrtezeitschrift fur Naturheilverfahren 40, 8 pp. 550-557.

M. Franchini, et al., Protective T-Cell-Based Imminity Induced in Neonatal Mice by a Single Replicative Cycle of Herpes Simplex Virus. (2001) Journal of Virology 75:83-89.

K. Stittelaar. et al. Protective Immunity in Macaques Vaccinated with a Modified Vaccinia Virus Ankara-Based Measles Virus Vaccine in the Presence of Passively Acquired Antibodies. (2000) Journal of Virology 74:4236-4243.

A. Mayr Zbl. Vet. Med. B, TC marker of the attenuated vaccinia vaccide strain "MVA" in human cell cultures and protective immunization against orthopox diseases in animals. (1976) 23:417-430.

A. Bot. et al. Induction of immunological memory in baboons primed with DNA vaccine as neonates. (2001) Vaccine 19:1960-70.

C. McLean. et al. Induction of a protective immune response by mucosa{ vaccination with a Disc HSV-1 vaccine. (1996) Vaccine 14:987-92.

M. Monteil.et al. Effective priming of neonates born to immune dams against the immunogenic pseudorabies virus glycoprotein gD by replication-incompetent adenovirus-mediated gene transfer at birth. (1997) Journal of General Virology 78:3303-10.

C. Siegrist Vacciniation in the neonatal period and early infancy. Int. Rev Immunol. 19:195-219, 2000.

I. Belyakov et al. Shared modes of protection against poxvirus infection by attenuated and conventional smallpox vaccine viruses. Proc. Natl. Acad. Sci. USA 100:9458-63, 2003.

MVA-BN: A safe and efficacious smallpox vaccine option. Advances in Life Science Feb. 2, 2002, http://www.advancesinlifescience.com/management 2.htm.

Roduit. et al. Immunogenicity and Protective Efficacy of Neonatal Vaccination against Bordetella petrussis in a Munine Model: Evidence for Early Control of Pertussis. Infection and Immunity, Jul. 2002, p. 3521-3528.

Engeirx®-B Lealfet of 9 May 2005, GlaxoSmithKline Biologicals Sa.

Moss. B. Geneically engineered poxviruses for recombinant gene expression, vaccination, and safety. Proc. Natl. Acad. Sci. USA 93:11341-11348, 1996.

Watts. et al., Nature Medicine 5:427-430, 1999.

Siegrist, Vaccine 19:3331-3346, 2001.

Siegrist, Vaccine 16:1473-1478, 1998.

Suarez. et al., Obstetrics & Gynecology100:87-93, 2002.

Bender. et al., Oral Immunization with a Replication-Deficient Recombinant Vaccinia Virus Protects Mice Against Inlfuenza. (1996) J. Virology, vol. 70(9):6418-6424.

In the matter of: Certain Modified Vaccinia Ankara ("MVA") Viruses and Vaccines and Pharmaceutical Compositions Based Thereon, Investigation No. 337-TA-550, Order No, 28: Denying in Part Complainants Motion for Summary Determination and Denying in Part Respondents Motion for Summary Determination, United States International Trade Commission, Washington, D.C., Apr. 18, 2006.

In the matter of: Certain Modified Vaccinia Ankara ("MVA") Viruses and Vaccines and Pharmaceutical Compositions Based Thereon, Investigation No. 337-TA-550, Nucleotide alignment of MVA-Antione vs Acambis 3000 MVA vs MVA-BN, Aug. 31, 2005.

In the matter of: Certain Modified Vaccinia Ankara ("MVA") Viruses and Vaccines and Pharmaceutical Compositions Based Thereon, Investigation No. 337-TA-550, Respondents Amended Pre-Hearing Brief, United States International Trade Commission, Washington, D.C., May 8, 2006.

In the matter of: Certain Modified Vaccinia Ankara ("MVA") Viruses and Vaccines and Pharmaceutical Compositions Based Thereon, Investigation No. 337-TA-550, Respondents Opposition to Compainant'S Motion for Sanctions, United States International Trade Commission, Washington, D.C.Jul. 7, 2006.

In the matter of: Certain Modified Vaccinia Ankara ("MVA") Viruses and Vaccines and Pharmaceutical Compositions Based Thereon, Investigation No. 337-TA-550, Respondent'S Opposition to Compainant'S Motion for Summary Determination of Infringement, 10439953.051603 United States International Trade Commission, Washington, D.C.

In the matter of: Certain Modified Vaccinia Ankara ("MVA") Viruses and Vaccines and Pharmaceutical Compositions Based Thereon, Investigation No. 337-TA-550, Respondent'S Rebuttal to Compainant'S Proposed Conclusions of Law, United States International Trade Commission, Washington, D.C., Jun. 14, 2006.

In the matter of: Certain Modified Vaccinia Ankara ("MVA") Viruses and Vaccines and Pharmaceutical Compositions Based Thereon, Investigation No. 337-TA-550, Compainant Bavarian Nordic'S Motion for Sanctions and Memorandum in Support of Its Motion, United States International Trade Commission, Washington, D.C., Jun. 21, 2006 (Public Version).

In the matter of: Certain Modified Vaccinia Ankara ("MVA") Viruses and Vaccines and Pharmaceutical Compositions Based Thereon, Investigation No. 337-TA-550, Memorandum in Opposition to Respondent'S Motion for Summary Determination, United States International Trade Commission, Washington, D.C., Mar. 30, 2006 (Public Version).

In the matter of: Certain Modified Vaccinia Ankara ("MVA") Viruses and Vaccines and Pharmaceutical Compositions Based Thereon, Investigation No. 337-TA-550, Compainant Bavarian Nordic'S Memorandum in Support of Its Motion in Limine, United States International Trade Commission, Washington, D.C., May 1, 2006 (Public Version).

In the matter of: Certain Modified Vaccinia Ankara ("MVA") Viruses and Vaccines and Pharmaceutical Compositions Based Thereon, Investigation No. 337-TA-550, Compainant'S Post Hearing Brief, United States International Trade Commission, Washington, D.C., April 28, 2006 (Public Version).

In the matter of: Certain Modified Vaccinia Ankara ("MVA") Viruses and Vaccines and Pharmaceutical Compositions Based Thereon, Investigation No. 337-TA-550, Compainant Bavarian Nordic's Motion for Summary Determination of Infringement of the '893 Patent. Its Memorandum of Law in Support of its Motion, its Statement of Undisputed Facts in Support of its Motion and Supporting Exhibits, United States International Trade Commission.

In the matter of: Certain Modified Vaccinia Ankara ("MVA") Viruses and Vaccines and Pharmaceutical Compositions Based Thereon, Investigation No. 337-TA-550, Compainant'S Post Hearing Reply Brief, United States International Trade Commission, Washington, D.C., June 14, 2006 (Public Version).

Bender. et al., Oral Immunization with a Replication-Deficient Recombinant Vaccinia Virus Protects Mice Against InIfuenza. (1996) J. Virology, vol. 70(9):6418-6424.

$JAX^{SM}$ Mice Data Sheet, Product Information for Stock No. 001913, The Jackson Laboratory, Bar Harbor, Maine, USA.

List of Documents Relied on in European Opposition Proceedings, two (2) pages.

Drillien. et al, Attenuation Profile Comparison of Various MVA Strains. Study Report, Institut de Génétique et de Biologie Moléculaire et Cellulaire, Illkirch, France, Feb. 22, 2006.

Hulsemann. et al.. Attenuation Profile Comparison of Various MVA Strains. Project #1050, Bavarian Nordic GmbH, Martinsried, Germany, Jan. 2006.

"Analysis of different strains of Modified Vaccinia virus Ankara (MVA) regarding their capability to grow and replicate in various cells lines." Vivacs Final Report, Project #1200104, Vivacs, GmbH, Martinsried, Germany.

Determination of various growth characteristics of different Vaccinia virus strains. Vivacs Study Plan, Project #0100506 and Vivacs Study Report, SR-0100506-01, Vivacs GmbH, Martinsried, Germany, Feb. 2006.

"Determination of various growth characteristics of different MVA strains." Vivacs Study Plan. Project #1200405, Vivacs Study Report, SR-1200405-00, Amendment to Vivacs Study Report. SR-Am-1200405-00, Amendment to Vivacs Study Report. SR-A1V102-1200405-00, Vivacs GmbH, Martinsried, Germany, Jan. 2006.

Zinkernagel. et al., "Attenuation Profile Comparison of Various MVA-strains." Study Report UA 02_06, University of Zurich, Zurich Switzerland, Mar. 2006.

Antione. G. "Differences in DNA sequence of MVA Acambis (AY603355) relative to MVA Antione et al (U94848)." Baxter Report -31/03/2006, Mar. 31, 2006.

Antione. et al., Corrigendum to "The complete genomic sequence of the Modified Vaccinia Ankara (MVA) strain: comparison with other orthopoxviruses" Virology 244 (1998) 365-396 BAXTER Bioscience, B008572.

"PCR-Amplification and Double Strand Sequencing of Five Genomic Regions of M4-MVA (U94848, NCBI Accession number)." Analytical Report, Project No. KN-639, GATC Biotech AG, Konstanz, Germany, May 9, 2006.

Sequence Report-MVA 572, Sequiserve, Vetterstetten, Germany, Jul. 6, 2006.

Sequence Report-MVA-1721, Sequiserve, Vetterstetten, Germany, Jul. 6, 2006.

* cited by examiner

Figure 2:

CD11c cells in 2 w old mice after MVA treatment

| Experiment BN9 | | blood | | blood | |
|---|---|---|---|---|---|
| | n | % CD11c | % CD11c CD8 | % CD11c | % CD11c CD8 |
| naïve | 3 | 3.5 | 0.4 | 4.9 | 1.3 |
| 1 Vaccination at birth | 3 | 7.4 | 2.1 | 16.1 | 2.0 |
| 1 vaccination at d7 | 4 | 21.5 | 17.0 | 4.4 | 17.6 |
| 2 vaccination d 0 and 7 | 4 | 42.7 | 35.6 | 27.9 | 25.7 |

Figure 5:

9 challenge experiments with HSV-1

|  | infected | survivors |
|---|---|---|
| Controls | 45 | 0 |
| MVA | 40 | 34 |

MODIFIED VACCINIA VIRUS ANKARA FOR THE VACCINATION OF NEONATES

This application is a continuation-in-part of application Ser. No. 11/341,955, filed Jan. 27, 2006, now abandoned, which is a continuation-in-part of application Ser. No. 10/418,854, filed Apr. 18, 2003, now U.S. Pat. No. 7,097,842, which is a continuation-in-part of Application No. PCT/EP01/13628, filed on Nov. 11, 2001, all of which are incorporated by reference.

SUMMARY OF THE INVENTION

The invention concern thes use of a virus for the preparation of a medicament for the vaccination or treatment of a neonatal or prenatal animal, including a human, wherein the virus is capable of infecting the cells of the neonatal or prenatal animal, including a human, but not capable of being replicated to infectious progeny virus in the neonatal or prenatal animal, including a human. The virus is preferably a Modified Vaccinia Virus Ankara.

In particular, the invention concerns the vaccination of neonates against infections with viruses belonging to the same virus group than the virus used for vaccination. Moreover, the invention concerns the vaccination of neonates against antigens selected from foreign antigens and tumour antigens, wherein the tumour antigen and/or the foreign antigen are different from the antigens associated with the virus. The invention further concerns the use of viruses as defined above to increase the level of factors which activate dendritic cells or their precursor cells and/or to increase the number of dendritic cells or their precursor cells and/or to increase the production and/or cellular content of an interferon (IFN) or IL-12.

BACKGROUND OF THE INVENTION

The natural environment of animals and human beings contains a large variety of infectious agents such as viruses, bacteria or fungi. Many of these infectious agents may cause diseases in the infected hosts. Under normal circumstances the infected host recovers from the disease induced by the infectious agent after a certain period of time. This recovery is due to the immune system of an animal or a human being.

The immune system is the part of the human or animal body that is responsible for eliminating the infectious agent. The immune response is divided into a specific and an unspecific (innate) reaction although both cooperate closely. The unspecific immune response is the immediate defence against a wide variety of foreign substances and infectious agents. In the innate immune response against viruses, Interferon (IFN)-α and IFN-β are absolutely essential to control the initial virus replication and to activate natural killer (NK) cells for immediate killing of infected cells. Intracellular bacterial or parasitic pathogens induce IL-12 that up regulates IFN-γ in NK cells and/or some T cell subsets. IFN-γ activated NK cells can now kill intracellular pathogens. Moreover, IFN-γ also activates macrophages and enables them to kill internalized pathogens.

By far the richest source of IFN-α/β on a per cell basis are dendritic cells (DC), a specialized cell population strategically distributed throughout the body. Plasmacytoid DC or CD11c$^+$ CD8$^+$ DC are among the best producers of IFN-α/β. CD8$^+$ DC that are infected with intracellular non-viral pathogens are the crucial cells able to secrete IL-12 essential for the early steps in immune defense.

A specific immune response can be induced against a particular foreign substance (antigen) after a lag phase, when the organism is challenged with this substance for the first time. The initiation of the specific immune response is coordinated by DC, too. There is a constant traffic of these cells from the periphery to the secondary lymphoid organs, the lymph nodes or spleen where naïve T and B cells recirculate. Antigen that is carried by DC to these organs enables activation of naïve T- and B cells to become effector T- and B cells. For this, DC not only carry the antigen, but the plasticity of pathogen recognition allows different gene activation in DC and thus a pathogen adjusted priming of T cells.

The specific immune response is highly efficient and is responsible for the fact that an individual who recovers from a specific infection is protected against this specific infection. Thus, a second infection with the same or a very similar infectious agent causes much milder symptoms or no symptoms at all, since there is already a "pre-existing specific immunity" to this agent. Such immunity and the immunological memory, respectively, persists for a long time, in some cases even lifelong. Accordingly, the induction of an immunological memory can be used for vaccination, i.e. to protect an individual against infection with a specific pathogen.

For vaccination the immune system is challenged with a vaccine which itself is less harmful than the pathogenic agent against which an immune response is to be induced. The vaccine comprises or expresses epitopes that are found in or expressed by the agent against which the vaccination is done. The organism, thus, is immunized against the agent containing the epitope that is part of the vaccine.

Typical vaccines are attenuated or inactivated viruses (e.g. the polio or small poxvirus vaccines), recombinant proteins (e.g. recombinant Hepatitis B virus S-protein), heat inactivated bacterial toxins (*Clostridium tetani* toxin) or polysaccharides of the bacterial capsule wall (*Streptococcus pneumoniae*).

Since infectious diseases might lead to very critical conditions in newborns and sucklings, there is an interest to vaccinate children or newborn animals as early as possible. Examples for conditions against which a vaccination is desirable are poxvirus infections, including smallpox. However, the attempts to successfully vaccinate newborns are hampered by the fact that the immune system of newborn mammals is not yet mature. The immune system of neonatal infants and mammalian animals is thought to mature gradually over a certain period of time. For humans the maturation occurs during the first year of life. This is the reason for the fact that the neonatal age group is left open to various infections during this first year (Gans et al., J. Am. Med. Assoc. (1998) 280, 527-532). More particularly, the neonatal infants have impaired B-cell function, deficiencies in primary antigen presentation by dendritic cells and limited T-cell proliferation (Gans et al., J. Am. Med. Assoc. (1998) 280, 527-532). Shortly after birth the levels of T cells in the spleen are 1,000 fold lower than in adults. In order to achieve at least a weak immunization it was suggested to use either replicating viruses or formulations comprising an adjuvant for immunization. However, with replication viruses there is always the risk that the immature immune system may become overwhelmed by virus infection or live viral vaccines since T cells are necessary for viral clearance (Hassett et al., J. Virol. (1997) 71, 7881-7888). Since there is a reduced production of cytokines by Th-1 helper T cells in neonates, the response by the infants is predominantly Th-2. Consequently, cytotoxic T cells are not recruited and viral clearance is not achieved.

The situation in mammalian animals is very similar to the situation in humans, i.e. the immune system after birth is not yet mature. In newborn mice, the number of splenic CD4+ T cells is 80.000 and that of CD8+ T cells 1000 fold lower than in spleens of adults. Moreover, the Interferon (IFN) producing system is immature in these mice. Therefore, neonatal mice are unable to efficiently control the expansion of intracellular pathogens by IFN at the site of infection. In addition, the low number and possibly inadequate activation stage of immune cells are too limited to cope with the rapidly expanding pathogens or replicating viruses used for vaccination.

Due to the risk associated with live viral vaccines it is not recommended to vaccinate neonatal animals, including humans, with replicating viruses. E.g. it is recommended not to vaccinate newborns against smallpox with the vaccinia virus strains that have been used until the eradication of smallpox, such as strains Elstee, Copenhagen and NYCBH. According to recent recommendations in the USA, babies younger than 12 months of age should not get the smallpox vaccines commercialized so far.

The vaccination of neonates with formulations comprising an adjuvant has the disadvantage that numerous harmful substances are introduced into the body. Thus, a vaccination in human neonates is only done in emergency cases, e.g. in case of the Hepatitis B virus infection.

In summary, it is to be noted that the immune system is not mature at birth. Since the vaccination with replication competent viruses or formulations comprising an adjuvant have significant disadvantages, infants are not vaccinated before the age of 2 months in Germany (Empfehlung der Ständigen Impfkommission STICO, 2001) or 6 weeks in the USA (ACIP "Recommended Childhood Immunization Schedule, United States").

The delay in the development of the immune system is compensated in part by the transfer of maternal antibodies from the mother to the suckling during pregnancy or by breastfeeding. However, not all infants are breastfeed due to various reasons. Thus, there is a very critical period of time of about 6-8 weeks in humans during which the infant having an immature and thus a not fully functional immune system does not receive maternal antibodies and during which a vaccination is usually not successful or too dangerous.

The situation is very similar in mammalian animals, in particular for economically important animals such as cows or companion animals such as cats and dogs. To reduce costs the amount of milk the calf receives from the mother is often drastically reduced. Instead the calf receives a mixture of milk powder, starter and specific concentrated feed, sometimes already in the first week after birth. Consequently, the calf does not receive the necessary amount and variety of maternal antibodies so that the immature immune system is very susceptible to infections. Furthermore, farmers who breed calves and those who raise them for meat production are often not the same. At 4 to 6 weeks of age calves from different breeder farms are pooled and shipped to other farms for meat production. At this time maternal antibodies are low and the immune system is not fully developed but the animals are exposed to new infectious agents under stress conditions. This increases the risk for infections that could be prevented by vaccination. A similar situation can be found in catteries or dog breeding facilities where the infectious pressure is high.

OBJECT OF THE INVENTION

It is the object of the present invention to provide means to vaccinate newborn humans and animals, respectively, against foreign antigens and antigens that are associated with diseases in humans and animals, respectively. More particularly, it is the object of the present invention to provide means allowing the accelerated maturation of the immune system of newborn animals and humans. It is a further object of the present invention to provide means that allow vaccinating neonatal animals, including humans, against poxvirus infections, in particular against smallpox.

DETAILED DESCRIPTION OF THE INVENTION

According to the present invention it was unexpectedly found that it is possible to safely and efficiently vaccinate and/or treat neonatal or prenatal animals, including humans, with viruses that are capable of infecting cells of the neonatal or prenatal animal, including a human, but not capable of being replicated in said cells to infectious progeny virus. In particular it has been shown that the viruses used according to the present invention, such as MVA, in particular MVA-BN and its derivatives (see below), can be administered to newborns without showing any harmful effects. The vaccination of the animal with the virus leads to a specific immune response against the virus used for vaccination and/or to a general vaccination against foreign antigens and tumour antigens as explained below in more detail. Moreover, the viruses used according to the present invention lead to an induction and/or enhancement of the maturation of the immune system, which is associated with an increase in the number of dendritic cells and factors such as Interferons. The vaccination with the viruses used according to the present invention is possible even if the formulation that is administered to the animal does not comprise an adjuvant.

In summary, the viruses that are used according to the present invention (i) elicit an effective immune response in neonates, (ii) can be administered without the need of an adjuvant and (iii) do not bear the risk of overwhelming the organism.

According to the present invention the protective effect is exerted for at least 5 days, preferably for at least 7, 14 or 28 days after the first vaccination.

Viruses that are "capable of infecting cells" are viruses harbouring on the viral surface structures capable of interacting with the host cells to such an extent that the virus or at least the viral genome becomes incorporated into the host cell. Although the viruses used according to the present invention are capable of infecting the host cell, they are not capable of being replicated to infectious progeny virus in the infected cells. In the context of the present invention the term "virus not capable of being replicated to infectious progeny virus in said cells" refers to viruses the genome of which is at least partially transcribed and translated into viral proteins or even replicated, however, not packaged into infectious viral particles. Thus, the viruses used according to the present invention are viruses leading to abortive infections in the host. Abortive infections may occur for two reasons: according to the first alternative a cell may be susceptible to infection but it may be nonpermissive for multiplication of the virus, e.g. due to the fact that not all necessary viral genes for multiplication of the virus in said cell are expressed and/or present in the viral genome. An example for this type of virus according to the present invention in human cells is Modified Vaccinia Virus Ankara (MVA), which is explained in more detail below. According to the second alternative an abortive infection may also result from infection of cells with defective viruses, which lack a full complement of viral genes. An example for such a virus according to the present invention for human cells is DISC-HSV1 (disabled single-cycle Herpes simplex virus), i.e. a Herpes simplex virus, which is restricted to a single cycle of infection (Dilloo et al., Blood 1997, 89: 119-127). This virus lacks the gene for the essential glycoprotein H (gH), but can be grown to high titer in a complementing cell line expressing gH. In noncomplementing cell lines that are permissive for herpesvirus growth, it is restricted to a single cycle of replication, leading to the release of noninfectious virus. The term "not capable of being replicated" refers preferably to viruses that do not replicate at all in the cells of the vaccinated animal. However, also those viruses are within the scope of the present application that show a minor residual replication activity that is controlled by the immature immune system of the neonate.

The virus according to the present invention may be any virus that is capable of infecting cells of the animal but not capable of being replicated to infectious progeny virus in said cells. It is to be understood, that a virus that is capable of infecting cells of a first animal species but not capable of being replicated to infectious progeny virus in said cells may behave differently in a second animal species. E.g., for humans MVA-BN and its derivatives (see below) are viruses that are capable of infecting cells of the human but that are not capable of being replicated to infectious progeny virus in human cells. The same viruses are very efficiently replicated in chickens, i.e. in chicken MVA-BN is not a virus that is capable of infecting cells of the chicken but not capable of being replicated to infectious progeny virus in said cells. It is known to the person skilled in the art which virus has to be chosen for a specific animal species. A test that allows to determine whether a virus is capable or not capable of being replicated in a neonatal or prenatal animal is disclosed in WO 02/42480 and uses the AGR129 mice strain. The results obtained in this mice model are indicative for humans. Thus, the term "not capable of being replicated to infectious progeny virus" as used in the present application corresponds to the term "failure to replicate in vivo" as used for mice in WO 02/42480. More details on this test are given below. The viruses according to the present invention are preferably capable of being replicated in at least one type of cells of at least one animal species. Thus, it is possible to amplify the virus prior to administration to the animal that is to be vaccinated and/or treated. By way of example reference is made to MVA-BN that can be amplified in CEF cells but that is a virus that is not capable of being replicated to infectious progeny virus in the neonatal or prenatal human. In this context it is to be noted that chemically or physically inactivated viruses do not have all the properties of this preferred embodiment since inactivated viruses are capable of infecting the cells of the neonatal or prenatal animal, including a human and not capable of being replicated to infectious progeny virus in the neonatal or prenatal animal, including a human, but these viruses are not capable of replicating in at least one type of cells of at least one animal species.

Preferably the virus is a DNA virus. More preferably, for mammalian cells, in particular for human cells, the DNA virus is selected from DISC-Hepesviruses and Modified Vaccinia virus Ankara (MVA).

Modified Vaccinia Ankara (MVA) virus is related to Vaccinia virus, a member of the genera Orthopoxvirus in the family of Poxviridae. MVA has been generated by 516 serial passages on chicken embryo fibroblasts of the Ankara strain of vaccinia virus (CVA) (for review see Mayr, A., et al. Infection 3, 6-14 [1975]). As a consequence of these long-term passages the resulting MVA virus deleted about 31 kilobases of its genomic sequence and, therefore, was described as highly host cell restricted to avian cells (Meyer, H. et al., J. Gen. Virol. 72, 1031-1038 [1991]). It was shown, in a variety of animal models that the resulting MVA was significantly avirulent (Mayr, A. & Danner, K. [1978] Dev. Biol. Stand. 41: 225-34). Additionally, this MVA strain has been tested in clinical trials as vaccine to immunize against the human smallpox disease (Mayr et al., Zbl. Bakt. Hyg. I, Abt. Org. B 167, 375-390 [1987], Stickl et al., Dtsch. med. Wschr. 99, 2386-2392 [1974]). These studies involved over 120,000 humans, including high risk patients, and proved that, compared to Vaccinia based vaccines, MVA had diminished virulence or infectiousness while it maintained good immunogenicity.

Preferred strains according to the present invention are MVA 575, deposited at the European Collection of Animal Cell Cultures (ECACC), Vaccine Research and Production Laboratory, Public Health Laboratory Service, Centre for Applied Microbiology and Research, Porton Down, Salisbury, Wiltshire SP4 0JG, United Kingdom, with the deposition number V00120707 and MVA-BN, deposited at the same institution with the deposition number V000083008, and derivatives thereof, in particular if it is intended to vaccinate/treat humans. Most preferred for humans is MVA-BN and its derivatives.

The properties of particularly preferred MVA strains, preferably the most preferred strains for humans, such as MVA-BN and its derivatives, can be summarized as follows:

(i) capability of reproductive replication in chicken embryo fibroblasts (CEF) and in the cell line BHK, but no capability of reproductive replication in the human cell line HaCaT, (ii) failure to replicate in vivo, (iii) induction of a higher immunogenicity compared to the known strain MVA 575 (ECACC V00120707) in a lethal challenge model and/or (iv) induction of at least substantially the same level of immunity in vaccinia virus prime/vaccinia virus boost regimes when compared to DNA-prime/vaccinia virus boost regimes.

The preferred MVA strains according to the present invention have the property (ii) failure to replicate in the organism, which is to be vaccinated or treated and/or in the corresponding test system as explained below and preferably one additional of the above properties, more preferably two additional of the above properties. Most preferred are MVA strains having all of the above properties. An example for an MVA strain having all of the above properties in humans is MVA-BN. Preferred derivatives of MVA-BN are derivatives having in addition to feature (ii) at least one of the above properties, more preferably at least two of the above properties. Most preferred are MVA-BN derivatives having all of the above properties.

For detailed information regarding to the assays used to determine whether a MVA strain has one or more of the above features (i) to (iv) reference is made to WO 02/42480. This publication also discloses how viruses having the desired properties can be obtained. In particular, WO 02/42480 provides a detailed definition of the features of MVA-BN and of a derivative of MVA-BN and discloses in detail the biological assays that are used to determine whether an MVA strain is MVA-BN or a derivative thereof. In other words, the features of MVA-BN, the description of biological assays allowing to evaluate whether a MVA strain is MVA-BN or a derivative thereof and methods allowing to obtain MVA-BN or a derivative thereof are disclosed in WO 02/42480. In the following it is shortly summarized how a person skilled in the art arrives in MVA strains having one or more of the above features and how he can test whether a given MVA strain has one or more of said features and is thus a most preferred virus according to the present invention. The following summary is not to be understood as to limit the relevance of WO 02/42480 for the present application to the following information. Instead, WO 02/42480 is herewith incorporated in its entirety by reference.

The term "not capable of reproductive replication" in the cell line HaCaT (Boukamp et al. 1988, J Cell Biol 106(3): 761-71) is used in the present application as defined in WO 02/42480. Thus, a virus that is "not capable of reproductive replication" in the cell line HaCaT is a virus that shows an amplification ratio of less than 1 in the human cell line HaCaT. Preferably, the amplification rate of the virus used as a vector according to the invention is 0.8 or less in the human cell line HaCaT. The "amplification ratio" of a virus is the ratio of virus produced from an infected cell (Output) to the amount originally used to infect the cells in the first place (Input) ("amplification ratio"). A ratio of "1" between Output and Input defines an amplification status wherein the amount of virus produced from the infected cells is the same as the amount initially used to infect the cells. The term "derivatives" of the viruses as deposited under ECACC V00083008 refers preferably to viruses showing essentially the same replication characteristics as the deposited strain but showing differences in one or more parts of its genome. Viruses having the same "replication characteristics" than the deposited virus are viruses that replicate with similar amplification ratios than the deposited strain in CEF cells and the cell lines BHK, HeLa, HaCaT and 143B and that show a similar replication in vivo as determined in the AGR129 transgenic mouse model (see below).

The term "failure to replicate in vivo" is used in the present application as defined in WO 02/42480. Thus, said term refers to viruses that do not replicate in humans and in the mice model as explained in WO 02/42480. The mice used in WO 02/42480 are incapable of producing mature B- and T-cells (AGR 129 mice). In particular MVA-BN and its derivatives do not kill AGR129 mice within a time period of at least 45 days, more preferably within at least 60 days, most preferably within 90 days after the infection of the mice with $10^7$ pfu virus administered intra peritoneally. Preferably, the viruses that show "failure to replicate in vivo" are further characterized in that no virus can be recovered from organs or tissues of the AGR129 mice 45 days, preferably 60 days and most preferably 90 days after the infection of the mice with $10^7$ pfu virus administered intra peritoneally. Instead of the AGR129 mice any other mouse strain can be used that is incapable of producing mature B and T cells and as such is severely immune compromised and highly susceptible to a replicating virus.

The details of the lethal challenge experiment used to determine whether a MVA strain has "a higher immunogenicity compared to the known strain MVA 575" are explained in WO 02/42480. In such a lethal challenge model unvaccinated mice die after the infection with replication competent vaccinia strains such as the Western Reserve strain L929 TK+ or IHD-J. The infection with replication competent vaccinia viruses is referred to as "challenge" in the context of description of the lethal challenge model. Four days after the challenge the mice are usually killed and the viral titer in the ovaries is determined by standard plaque assays using VERO cells. The viral titer is determined for unvaccinated mice and for mice vaccinated with MVA-BN and its derivatives. More specifically MVA-BN and its derivatives are characterized in that in this test after the vaccination with $10^2$ TCID$_{50}$/ml virus the ovary virus titers are reduced by at least 70%, preferably by at least 80%, more preferably by at least 90% compared to unvaccinated mice.

In a preferred embodiment the viruses according to the present invention, such as MVA, in particular MVA-BN and its derivatives, are useful for prime/boost administration. The viruses, in particular MVA strains that are most preferably used in the present invention, such as MVA-BN and its derivatives as well as corresponding recombinant viruses harbouring heterologous sequences, can be used to efficiently first prime and then boost immune responses in native animals as well as in animals with a pre-existing immunity to poxviruses. Thus the most preferred virus according to the present invention induces at least substantially the same level of immunity in vaccinia virus prime/vaccinia virus boost regimes compared to DNA-prime/vaccinia virus boost regimes.

A vaccinia virus, in particular an MVA strain is regarded as inducing at least substantially the same level of immunity in vaccinia virus prime/vaccinia virus boost regimes when compared to DNA-prime/vaccinia virus boost regimes if the CTL response as measured in one of the "assay 1" and "assay 2" as disclosed in WO 02/42480, preferably in both assays, is at least substantially the same in vaccinia virus prime/vaccinia virus boost regimes when compared to DNA-prime/vaccinia virus boost regimes. More preferably the CTL response after vaccinia virus prime/vaccinia virus boost administration is higher in at least one of the assays, when compared to DNA-prime/vaccinia virus boost regimes. Most preferably the CTL response is higher in both assays.

The virus used according to the present invention may be a non-recombinant virus, such as MVA, i.e. a virus that does not contain heterologous nucleotide sequences. An example for a non-recombinant vaccinia virus is MVA-BN and its derivatives. Alternatively the virus may be a recombinant virus, such as a recombinant MVA that contains additional nucleotide sequences, which are heterologous to the virus.

The term "heterologous" as used in the present application refers to any combination of nucleic acid sequences that is not normally found intimately associated with the virus in nature, such virus is also called "recombinant virus".

The heterologous nucleic acid sequence is preferably selected from a sequence coding for at least one antigen, antigenic epitope, beneficial proteins and/or therapeutic compound.

The term "beneficial proteins" as used in the present application refers to any proteins that are helpful in protecting an animal against an antigen selected from tumour antigen and foreign antigen, wherein the tumour antigen and the foreign antigen is different from the antigens associated with the virus. Alternatively and more particulary the "beneficial proteins" are active in increasing the level of factors which activate dendritic cells and/or active in increasing the number of dendritic cells and/or active in increasing the production and/or cellular content of an interferon (IFN) or IL-12. Thus, examples for such beneficial proteins are interferons such as IFN-alpha or IFN-beta, IL-12, Flt-3-L and or GM-CSF.

The antigenic epitopes may be any epitopes to which it makes sense to induce an immune response. Examples for antigenic epitopes are epitopes from *Plasmodium falciparum*, Mycobacteria, Influenza virus, from viruses selected of the family of Flaviviruses, Paramyxoviruses, Hepatitis viruses, Human immunodeficiency viruses or from viruses causing hemorrhagic fever such as Hantaviruses or Filoviruses, i.e., Ebola or Marburg virus. Thus, if e.g. a recombinant MVA expressing heterologous epitopes is used to vaccinate neonates according to the present invention, the result of this treatment is not only a general vaccination due to the accelerated maturation of the immune system but also a specific vaccination against the heterologous epitope expressed from the heterologous MVA.

A "therapeutic compound" encoded by the heterologous nucleic acid in the recombinant virus can be, e.g., a therapeutic nucleic acid such as an antisense nucleic acid or a peptide or protein with desired biological activity.

The insertion of heterologous nucleic acid sequence is preferably into a non-essential region of the virus genome. Alternatively, the heterologous nucleic acid sequence is inserted at a naturally occurring deletion site of the viral genome (for MVA disclosed in PCT/EP96/02926). Methods how to insert heterologous sequences into the viral genome such as a poxviral genome are known to a person skilled in the art.

The present invention also provides a pharmaceutical composition and a vaccine comprising a virus according to the present invention, such as MVA, e.g., for inducing an immune response in a living animal body, including a human.

The pharmaceutical composition may generally include one or more pharmaceutical acceptable and/or approved carriers, additives, antibiotics, preservatives, adjuvants, diluents and/or stabilizers. Such auxiliary substances can be water, saline, glycerol, ethanol, wetting or emulsifying agents, pH buffering substances, or the like. Suitable carriers are typically large, slowly metabolized molecules such as proteins, polysaccharides, polylactic acids, polyglycollic acids, polymeric amino acids, amino acid copolymers, lipid aggregates, or the like.

For the preparation of vaccines, the virus or its recombinants is converted into a physiologically acceptable form. Such methods are known to the person skilled in the art. For MVA and other poxviruses the vaccine can be prepared based on the experience in the preparation of poxvirus vaccines used for vaccination against smallpox (as described by Stickl, H. et al. [1974] Dtsch. med. Wschr. 99, 2386-2392). For example, the purified virus is stored at −80° C. with a titre of $5 \times 10^8$ TCID$_{50}$/ml formulated in about 10 mM Tris, 140 mM NaCl pH 7.4. For the preparation of vaccine shots, e.g., $10^1$-$10^8$ particles of the virus such as MVA are lyophilized in 100 ml of phosphate-buffered saline (PBS) in the presence of 2% peptone and 1% human albumin in an ampoule, preferably a glass ampoule. Alternatively, the vaccine shots can be produced by stepwise freeze-drying of the virus in a formulation. This formulation can contain additional additives such as mannitol, dextran, sugar, glycine, lactose or polyvinylpyrrolidone or other additives such as antioxidants or inert gas, stabilizers or recombinant proteins (e.g. human serum albumin) suitable for in vivo administration. The glass ampoule is then sealed and can be stored between 4° C. and room temperature for several months. However, as long as no need exists the ampoule is stored preferably at temperatures below −20° C.

For vaccination or therapy the lyophilisate can be dissolved in 0.1 to 0.5 ml of an aqueous solution, preferably physiological saline or Tris buffer, and administered either systemically or locally, i.e. by parenterally, intramuscularly or any other path of administration know to the skilled practitioner. The mode of administration, the dose and the number of administrations can be optimized by those skilled in the art in a known manner.

The virus according to the present invention, in particular MVA can be administered by oral, nasal, intramuscular, intravenous, intraperitoneal, intradermal, intra-utero and/or subcutanous application. In small animals the inoculation for immunization is preferably performed parenterally or nasaly, whereas in larger animals or humans a subcutaneous, intramuscular or oral inoculation is preferred.

MVA is administered preferably in a dose of $10^1$ TCID$_{50}$ (tissue culture infectious dose) to $10^9$ TCID$_{50}$.

As pointed out above the virus according to the present invention, in particular MVA, such as MVA-BN and its derivatives may be administered in a therapeutically effective amount in a first inoculation ("priming inoculation") and in a second inoculation ("boosting inoculation").

In the context of the present invention the term "animal" covers also human beings. More generally, the animal is a vertebrate animal, preferably a mammalian animal including a human. Specific examples for animals are pets such as dogs, cats, economically important animals such as calves, cattle, sheep, goats, horses, pigs and other animal such as mice, rats. For these animal species and for humans MVA and DISC-HSV are particularly preferred viruses. The invention may also be used for economically important birds such as turkeys, ducks, goose and hens if viruses are used that are capable to infect the bird's cells but not capable of being replicated to infectious progeny virus in said cells.

The term "domestic animals" as used in the present description refers preferably to mammalian domestic animals, more preferably to dogs, cats, calves, cattle, sheep, goat, pigs, horses, deer.

According to a first alternative the viruses according to the present invention, in particular MVA-BN and its derivatives may be used as specific vaccines, i.e. to elicit an immune response that protects the vaccinated newborn against diseases caused by a virulent virus belonging to the same virus group, family or genus than the virus that was used for vaccination. By way of example MVA as defined above, in particular MVA-BN and its derivatives can be used to vaccinate newborn humans against poxvirus infections, in particular against smallpox. MVA, in particular MVA-BN and its derivatives, may also be used to vaccinate vertebrate animals against poxvirus infections of veterinary importance. According to this first alternative the virus used for vaccination may be a non-recombinant virus, such as MVA-BN or its derivatives, or a recombinant virus harboring genes in the viral genome that are not naturally found in said genome. Preferably, the recombinant virus harbors additional genes that are helpful in stimulating the immune response. Examples for this kind of genes are cytokine genes and interferon genes.

According to a second but related alternative neonates are vaccinated with a recombinant virus harboring a heterologous nucleic acid sequence as defined above to induce an immune response against the amino acid sequence expressed from the heterologous nucleic acid sequence. By way of example the nucleic acid sequence may code for an antigen or an antigenic epitope as defined above. Examples for a recombinant virus according to this embodiment are recombinant MVA, in particular recombinant MVA-BN or a derivative thereof, comprising a heterologous nucleic acid coding for antigens from (i) viruses other than MVA, such as HIV-1, HIV-2, Denguevirus, West-Nile Virus, Japanese Encephalitis virus, measles virus, (ii) tumour antigens, (iii) bacteria, (iv) fungi. If the antigen expressed from the recombinant virus is e.g. an HIV antigen it is possible to use the recombinant virus to induce an immune response in the vaccinated neonate against HIV and to prevent AIDS. In a broader sense the recombinant virus expressing the antigen or antigenic epitope is used to induce an immune response against the agent from which the heterologous sequence is derived and/or against the agent that comprises the antigen or antigenic epitope.

According to a third alternative it has been unexpectedly found that viruses that are capable of infecting the cells of the neonatal or prenatal animal, including a human, but not capable of being replicated to infectious progeny virus in the neonatal or prenatal animal, including a human can be used for the preparation of a medicament for protecting an animal, in particular a newborn animal, including a human, against an antigen selected from tumour antigen and foreign antigen, wherein the tumour antigen and/or the foreign antigen are different from the antigens associated with the virus.

According to this third alternative newborns vaccinated with the viruses according to the present invention, in particular with MVA, such as MVA-BN and its derivatives, are protected against a challenge with foreign antigens such as infectious agents. Thus, the viruses according to the present invention, in particular MVA are a general vaccine for newborns, i.e. by vaccinating newborns with the viruses according to the present invention, in particular MVA the immune system of the newborns becomes more competent to deal with foreign antigens such as viruses. In the example section this is exemplified for vaccination with MVA and a subsequent challenge with Herpes simplex virus type 1. Thus, if the virus according to the present invention, in particular MVA is used for the vaccination of newborns the vaccinated animals are more protected against foreign antigens than unvaccinated animals in the critical time span until a functional and mature immune system is established.

According to the present invention "the tumour antigen and/or the foreign antigen is different from the antigens associated with virus". This term is to be interpreted in that according to this embodiment the invention is not primarily intended to use a virus such as MVA to induce an immune response against the virus itself. Instead the virus is used to induce a immune response or at least a general immune stimulation that protects the host against foreign antigens and tumour antigens, respectively, that are not associated with the virus. The term "antigens associated with the virus" refers to epitopes and antigens of the virus particle and to antigens and epitopes on the surface of a cell infected with the virus that are the result of the expression of the viral genome.

In the context of this embodiment the term "foreign antigens" refers to any antigens and epitopes that are not naturally a part or a component of the animal body. Foreign antigens are especially antigens and epitopes from infectious agents and toxins, Typical infectious agents are viruses such as herpesviruses, retroviruses, rabiesviruses, rhabdoviruses, adenoviruses; bacteria such as Salmonella, Mycoplasm, Meningicoccus, Hemophilus; prions or fungi.

The invention is not only of interest to vaccinate animals against foreign antigens but, in an alternative embodiment, is also suitable to vaccinate against tumour antigens. "Tumour antigens" are antigens associated with certain tumoural diseases. Tumour antigens are most often antigens encoded by the genome of the host that develops the tumour. Thus, in a strict sense tumour antigens are not foreign antigens. However, tumour antigens are found in significant amounts in tumours, whereas the amount of tumour antigens in normal tissues is significantly lower and most often no tumour antigens are found at all in normal tissue. Examples for tumour antigens are known to the person skilled in the art and include e.g. the MAGE antigens. MVA is effective against these tumour antigens since the vaccination of animals leads to an activation and/or accelerated maturation of the immune system which then may lead to the destruction of tumour cells.

The term "protecting against an antigen" refers to the development of an immune response, which is directed against the foreign or tumour antigen. If the foreign antigen is an infectious agent the host is protected against said agent, i.e. the host develops an immune response against said antigen. Consequently, the infection with the infectious agent leads to a less severe disease or to no disease at all. The term "protecting" is not to be understood in the sense that there is always a 100% protection against the foreign or tumour antigen. Instead, the term "protection" as used in the present application refers to any beneficial effect that helps the animal to deal with the foreign antigen and the tumour antigen, respectively.

According to the present invention such a protective effect is exerted for at least 5 days, preferably for at least 7, 14 or 28 days after the first vaccination. In other words, the vaccinated and or treated animal is protected e.g. against a foreign antigen if the animal comes into contact with said antigen after 5, 7, 14 and 28 days, respectively.

In the context of the present invention the effect of the vaccination of newborns with the virus according to the present invention, in particular with MVA may be explained by the induction or enhancement of maturation of the immune system and/or the activation of the immune system. In the context of the present invention the term "induction or enhancement of the maturation of the immune system" refers inter alia to the accelerated increase of dendritic cells or their precursors in vaccinees relative to controls. The terms "acceleration of the maturation" of the immune system an "enhancement of the maturation" of the immune system are used interchangeably in this description.

The "activation of the immune system" is characterized by the expression on the surface of cells of molecules and hormones that ease cell/cell interaction or trafficking and/or by the secretion of said molecules and hormones by the cells. Specific receptors take up these signals and respond. Activation markers are inter alia Flt3-L, IL-12, IFN-alpha, MHC-II and CD8, in particular CD8alpha (see below).

The accelerated development/maturation of the immune system is correlated with an increase of the level of factors activating and or mobilizing dendritic cells (DC) or their precursor cells and/or an increase in the number of dendritic cells and their precursor cells and/or an increase in the production and/or cellular content of an interferon or IL-12. An example for DC precursor cells that are induced by the virus according to the present invention, in particular by MVA, are plasmacytoid DC precursors that are very important for the defence against viral infections and that seem to produce IFN α/β.

More specifically, the enhancement of the maturation of the immune system is preferably defined by an at least 2-fold increase in surface markers found on DC, such as MHC-II, CD40 and/or CD80/86. Preferably such an increase may be measured in the blood. Further markers to characterize an enhancement of the maturation of the immune system are Flt3-L, IL-12, IFN-alpha, MHC-II and CD8a (see below). Moreover, the accelerated maturation of the immune system is preferably correlated to an at least 1.5 fold increase, preferably an at least 2.0 fold increase in the number of CD11c positive cells in the blood and/or the spleen 7 days after the administration of MVA-BN to newborn animals compared to control animals that have not received MVA-BN. Moreover, the enhancement of maturation of the immune system may preferably be correlated with an at least 1.5 fold increase, more preferably an at least 2.0 fold increase of the concentration of Flt3-L two days after the vaccination of neonates with viruses according to the present invention, when compared to age matched controls.

In this context it is to be noted that there is an association between the phenotype and function of murine and human DC populations that can be characterised by their surface phenotype (Hochrein et al. 2002. *Hum. Immunol.* 63: 1103). DC in the blood can be detected using flow cytometry using a range of surface markers (MacDonald et al. 2002. *Blood.* 100:4512) that also allow specific populations of DC, such as the plasmactoid DC to be identified (Dzionek et al. 2002. *Hum Immunol.* 63: 1133; Dzionek et al 2000. *J. Immunol* 165:

6037). Using similar techniques DC can also be detected in other human tissues (Summers et al. 2001. *Am. J. Pathol.* 159: 285).

According to the present invention the viruses as defined above might also be used to treat neonatal or prenatal animals to increase the level of factors activating and or mobilizing dendritic cells (DC) or their precursor cells and/or an increase in the number of dendritic cells and their precursor cells and/or an increase in the production and/or cellular content of an interferon or IL-12. It has been demonstrated that following vaccination with MVA-BN the plasmacytoid dendritic cells make significantly more IL-12 and have an increased IFN-alpha production and upregulation of MHC-II and CD8a. The increase of IL-12 after the administration of the viruses used according to the present invention is preferably 2 times, more preferably 100 times, 500 times, 1000 times, 2500 times or 5000 times. The increase of the concentration of Flt3-L two days after the vaccination of neonates with viruses according to the present invention, most preferably with MVA-BN or its derivatives, is preferably 1.5 fold, more preferably 2.0 fold when compared to age matched controls.

The term "activation of dendritic cells or their precursors" refers to the maturation of DC to antigen presenting cells through ill-defined cell stages driven by hormones and stimuli. The intermediates of DC are termed precursors. These immature DC reach the periphery. Different (antigenic) stimuli activate DC. Activation markers, which are upregulated in activated dendritic cells are inter alia Flt3-L, IL-12, IFN-alpha, MHC-II and CD8a (see below).

It was noted that hormones such GM-CSF lead to more immature DC in the periphery. Because GM-CSF leads to more DC precursor in bone marrow, blood and peripheral organs (and the cells have to move there), this phenomenon has been termed "mobilization of dendritic cells or their precursors". This definition is also used in the present description.

Consequently, the vaccination of animals including a human is especially useful, if it is intended to increase the level of factors activating dendritic cells (DC) or their precursor cells and/or to increase the number of dendritic cells or their precursor cells and/or to increase the production and/or cellular content of an interferon or IL-12.

Factors that activate dendritic cells comprise inter alia Flt3-L (Lyman et al., Cell 1993, 75: 1157-1167) and GM-CSF. Typical interferons according to the present invention are IFN-alpha and IFN-beta. The viruses used according to the present invention induce Flt3-L and it is assumed that some of the beneficial effects observed are due to said induction.

In the context of the present application a newborn animal or human is defined as a animal or human not yet having a mature immune system. Throughout this specification the terms "newborn animal" and "neonatal animal" are used synonymously. A mature immune system is characterized by the ability to fully activate the innate immune system and by the fact that all known T and B cell functions and products are in place, in particular immunoglobulin isotypes such as IgA and IgE. Thus an immature immune system is characterized by a low number of T cells, B cells and dendritic cells relative to adults, by an IFN production which is low compared to adults and by the fact that the secondary lymphoid organs are not fully mature. More specifically a "neonatal" or "newborn" in the context of the present invention may be defined as an infant animal having a number of splenic CD4+ cells being preferably at least 2-fold, more preferably at least 20-fold, more preferably at least 200 fold, more preferably at least 2,000 fold, most preferably at least 20,000 fold lower than the average number of splenic CD4+ cells in adults- In mice the immune system is mature at the age of 4 weeks. In humans maturity is probably 6 month to 1 year. In cats and dogs the immune system is mature usually at the age of 6 month, in calves, sheep and pigs at the age of 4-12 weeks. The vaccination with the virus according to the present invention, in particular with MVA is preferably done during before the immune system is mature. However, since maturity develops almost exponentially after birth it is most preferred to vaccinate with the virus according to the present invention, in particular with MVA as early after birth as possible. Since in all relevant domestic animals and in humans the immune system is mature not earlier than 4 weeks after birth, it is generally preferable that vaccination with the virus according to the present invention, in particular with MVA, is done preferably within 4 weeks after birth, more preferably within 2 weeks after birth, even more preferably within 1 week after birth, most preferably within 3 days after birth. These general terms are applicable to all important domestic animals, in particular to all important domestic mammalian animals, including humans. The person skilled in the art will be aware of the fact that even older animals may be regarded as newborns/neonatals in the context of the present invention and that, thus, the vaccination may also be successfully carried out with older animals, when the immune system is not yet mature 4 weeks after birth. Thus, in humans the vaccination may be carried out within 6 month after birth, more preferably within 3 month after birth, more preferably within 2 month after birth, more preferably within 4 weeks after birth, more preferably within 2 weeks after birth, even more preferably within 1 week after birth, most preferably within 3 days after birth.

Since the best effects of the virus according to the present invention, in particular MVA as a general vaccine are observed if the virus is administered to an immature immune system, it might be preferred to vaccinate even prenatal animals including humans. Prenatal vaccination may be desirable in economically important animals such as cattle or pigs. If the placenta lets through the virus the prenate can be vaccinated simply by vaccinating the mother animal. Thus, the vaccination of the mother animal to vaccinate the prenate is particularly promising in an animal having a placenta endotheliochorialis, such as dogs, cats, rats and mice or having a placenta heamochorialis, such as primates including humans. In animals having a placenta chorionepithelialis, such as cattle and sheep or having a placenta syndesmochorialis, such as pigs and horses, the vaccination of prenates can be preferably done by in utero administration. Of course, this mode of administration can be also done for animal having a placenta endotheliochorialis or haemochorialis.

Since the viruses according to the present invention, in particular MVA lead to an accelerated maturation of the immune system and since the viruses according to the present invention, in particular MVA are thus useful as a general vaccine, the vaccinated animals are protected against a variety of diseases. More specifically the viruses according to the present invention, in particular MVA can be used to vaccinate cats for general well being and against feline herpes or feline infectious peritonitis. The viruses according to the present invention, in particular MVA may be used in dogs for general well being and against respiratory tract associated (viral) diseases. The viruses according to the present invention, in particular MVA may be used in pigs for general well being and against Hemophilus or Mycoplasm infections, especially in fattening pigs.

As pointed out it is a preferred embodiment to use the viruses according to the present invention, in particular MVA, in newborns or prenatal animals to protect said animal against a foreign antigen and/or a tumour antigen, wherein the tumour antigen is different from the antigens associated with the virus used for vaccination. However this embodiment is not restricted to newborn and prenatal animals. Instead, in an alternative embodiment the invention can be carried out for animals of all ages, since a beneficial effect can be observed also in adult animals. Thus, according to this embodiment the viruses as defined above, in particular MVA-BN and its derivatives are useful to protect an animal, including a human, against an antigen selected from tumour antigen and foreign antigen, wherein the tumour antigen and/or the foreign antigen is different from the antigens associated with the virus. As pointed out above, the viruses used according to the present invention are capable of infecting cells of the animal but not capable of being replicated to infectious progeny virus in said cells. All information, definitions, including the definition of the duration of the protective effect, examples as well as the preferred, more preferred and most preferred embodiments given above for neonates also apply for the present embodiment according to which the virus may also be administered to adults.

In contrast to newborns, the immune system of adult animals has already matured. Nevertheless, it might be that the immune system is weakened due to certain diseases or simply due to the age of the animal. Especially in immune-compromised people and in elderly people the administration of the viruses according to the present invention, in particular MVA to the animal may have a beneficial effect inter alia by increasing the level of factors activating and/or mobilizing dendritic cells (DC) or their precursor cells and/or by increasing the number of dendritic cells or their precursor cells and/or by increasing the production and/or cellular content of an interferon or IL-12. Thus, even in adult animals the administration of the viruses according to the present invention, in particular MVA may lead to an increased competence of the immune system to deal with foreign antigens and/or tumour antigens. In other words, the viruses used according to the present invention are useful for the activation of the immune system in general.

The invention further concerns the viruses according to the present invention, in particular MVA for the preparation of a medicament to be administered to an animal, including a human, wherein said medicament increases the level of factors which activate dendritic cells and/or increases the number of dendritic cells and/or increases the production and/or cellular content of an interferon (IFN) or IL-12. All definitions given above for the other embodiments are also applicable for the present embodiment. According to this embodiment the invention does not aim primarily at inducing a protection against foreign antigens and/or tumour antigens. Instead, this embodiment is aimed at treating conditions and diseases characterized by a low level of factors which activate dendritic cells and/or by a insufficient or too low number of dendritic cells and/or by a low production and/or cellular content of an interferon (IFN) or IL-12. Thus, according to this embodiment the treatment with the viruses according to the present invention, in particular MVA could protect against allergies or autoimmune diseases. Again this treatment is particularly promising if the viruses according to the present invention, in particular MVA are administered to newborn animals.

Additionally, according to a further embodiment the virus according to the present invention, such as MVA, in particular MVA-BN and its derivatives, is particularly useful to induce immune responses in immuno-compromised animals, e.g., monkeys (CD4<400/μl of blood) infected with SIV, or in immuno-compromised humans. The term "immuno-compromised" describes the status of the immune system of an individual, which shows only incomplete immune responses or has a reduced efficiency in the defence against infectious agents.

The invention further concerns a method for protecting an animal, including a human, against an antigen selected from tumour antigen and foreign antigen, by administration of a virus according to the present invention, in particular Modified Vaccinia virus Ankara (MVA), wherein the tumour antigen and/or the foreign antigen is different from the antigens associated with the virus.

In a further embodiment the invention concerns a method for the treatment of an animal, including a human, to increase the level of factors which activate dendritic cells and/or to increase the number of dendritic cells and/or increase the production and/or cellular content of an interferon (IFN) or IL-12, comprising the administration of a Modified Vaccinia virus Ankara (MVA).

SHORT DESCRIPTION OF THE FIGURES

FIG. 1A: Newborn mice were injected once within 24-48 h of birth with $10^6$ p.f.u. of MVA or DISC HSV-1 or treated with physiological saline (NaCl) as controls. At 7 days of age, CD11c, a pan DC marker was used to determine these cells in peripheral blood by flow cytometry. Mean and standard deviation of 3 to 5 experiments are shown.

Figure 1B:
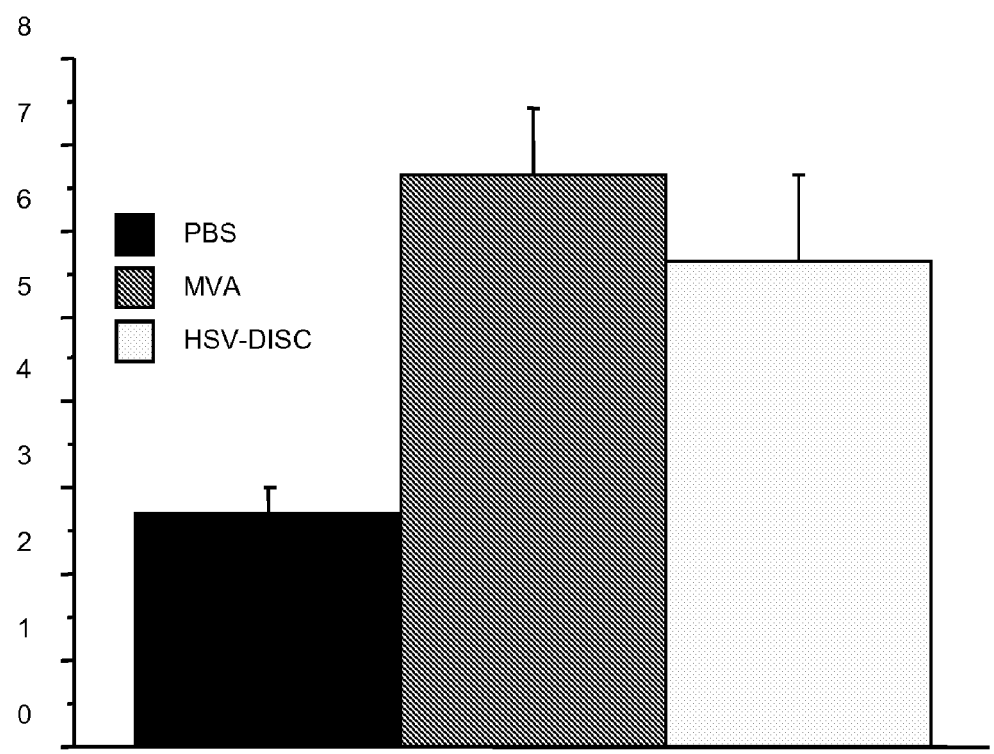

FIG. 1B: Experiment as in FIG. 1A. However, CD11c cells were determined in spleen by flow cytometry FIG. 1C: Experiment as in FIG. 1A. However, CD11c cells were determined in peritoneal fluid by flow cytometry FIG. 2: Mice were vaccinated with MVA-BN as indicated in the left column. After two weeks the percentage of CD11c$^+$ single and CD11c$^+$/CD8$^+$ double positive cells in spleen and in blood were determined by flow cytometry.

Figure 3:
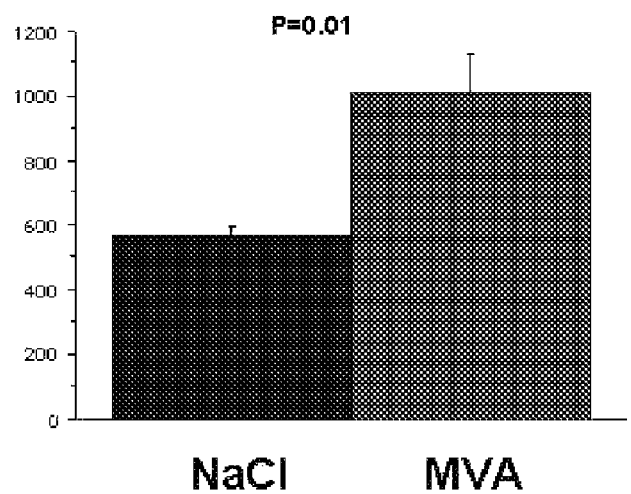

FIG. 3: Newborn mice were injected with MVA or NaCl as control at day one and 5 of age. At day 8, murine Flt3-L was determined in serum of these mice by ELISA and the values are given as pg/ml.

Figure 4:
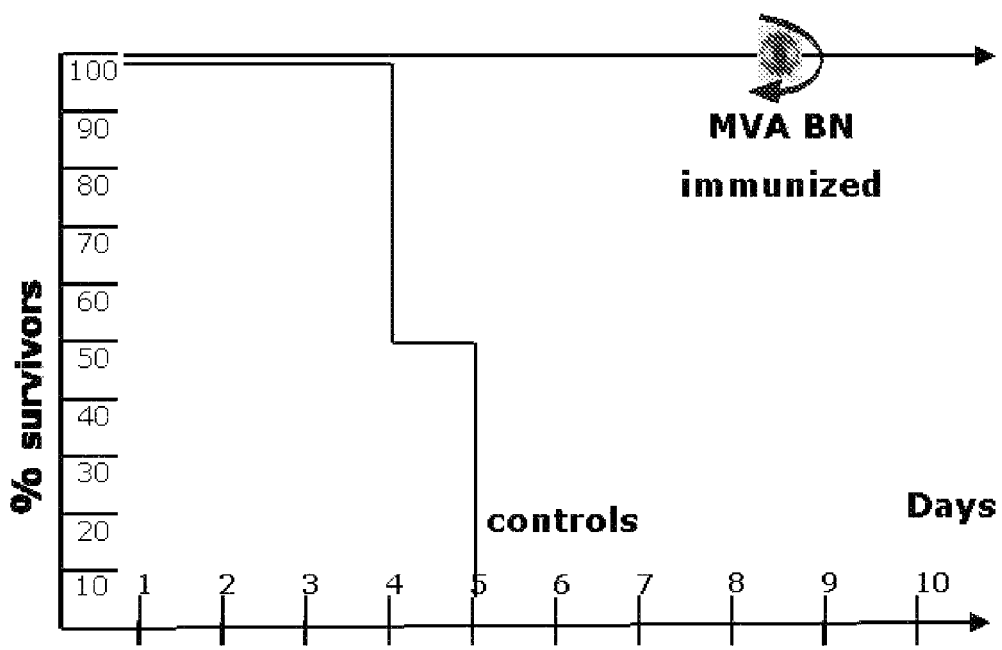

FIG. 4: Newborn mice were injected once within 24-48 h of birth with $10^6$ p.f.u. of MVA or treated with NaCl as controls. At 7 days of age, all mice were exposed to 100×LD$_{50}$ of HSV-1 strain F. The number of surviving animals was monitored for 21 days.

FIG. 5: Mice were treated as in FIG. 4. The data represent 9 different challenge experiments with 100 LD$_{50}$ of HSV-1. None of the control animals survived the challenge.

Figure 6:
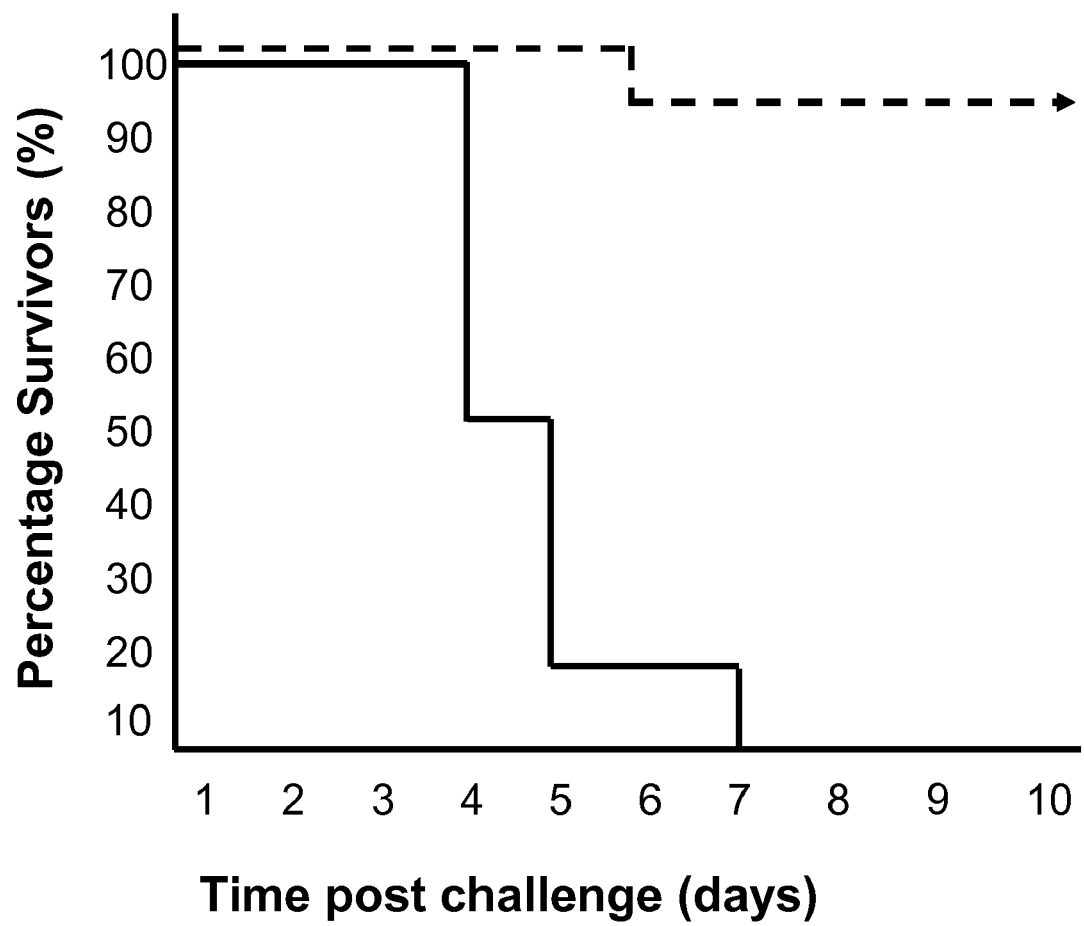

FIG. 6: Survival of adult mice vaccinated on the first day of life with MVA-BN following a lethal vaccinia challenge. Three litters of 6 1-day-old pups (18 mice) were vaccinated with MVA-BN ($2.5 \times 10^7$ TCID$_{50}$) and at 4 weeks (adult mice) challenged with a lethal dose of vaccinia. MVA-BN vaccination clearly induced a protective immunity in neonatal mice that lasted until adulthood.

EXAMPLES

The following examples will further illustrate the present invention. It will be well understood by a person skilled in the art that the provided examples in no way may be interpreted in a way that limits the applicability of the technology provided by the present invention to this examples.

Example 1

(i) MVA-BN and DISC-HSV Induces Dc of the CD11c+ and CD8+ Phenotype in Newborn Animals First set of experiments: Newborn mice are naturally immunodeficient because the IFN system is not mature. The number and activation state of DC, the best producers of IFN know today has not been analyzed. DC can be induced in vitro as well as in vivo by a variety of stimuli. In these studies it was tested whether a controlled MVA-BN replication could induce DC and analyzed their phenotype. Groups of mice were injected with $10^6$ plaque forming units (p.f.u.) of MVA-BN or saline only within 1-2 days after birth and in some cases 5 days after birth. Blood and spleen cells from individual mice of both groups were analyzed by FACS and the data compared.

Data from 7 to 8 individual mice indicated that treatment with MVA-BN increased CD11c+ cells 2-3 fold accompanied with increased expression of MHC 11 and increased presence of T cells of the CD4 or CD8 type Interestingly, CD19/54, a marker for mature B cells decreased indicating that these cells emigrated in organs other than spleen or that precursor of B cells were recruited early to other lineages notably DC of the plasmacytoid phenotype that carries early B cell markers (B220).

Data from three different experiments indicated reproducibility and significant differences. Experiments with DISC-HSV-1, a different replication controlled viral vaccine, induces similar amounts of CD11c+ cells after neonatal priming.

Figure 1C:
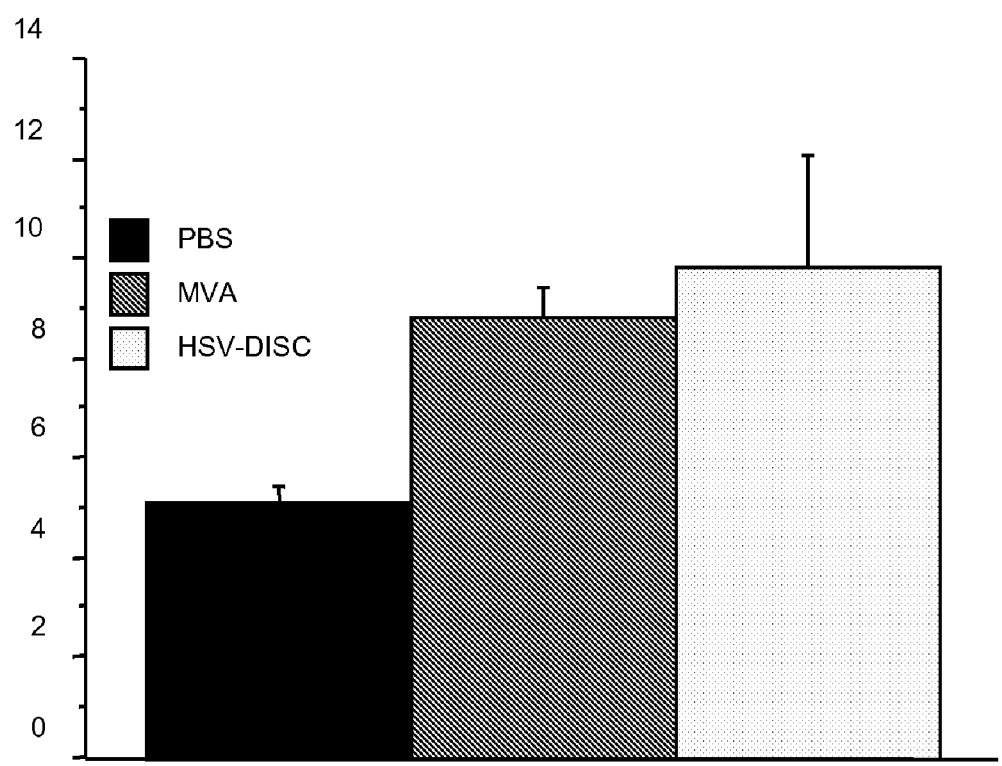

The results are summarized in FIG. 1A-C.

To further investigate subpopulations of DC in blood and spleen and analyze long-term effect of treatment with MVA-BN, cells in blood and spleen were analyzed at 2 weeks of age. At this time point, treated animals had about twice the number of CD11c+ cells in spleen than at one week of age but a single treatment with the virus at birth lead to a 3 fold elevated number of these cells in spleen 2 weeks later (FIG. 2). Similar effects were seen in blood with the exception that CD11c+/CD8a+ were about 4 times higher. A single treatment with MVA-BN at 7 days of birth lead to an increase of CD11c+/CD8a+ from 13 to 40 fold with a less dramatic effect on the CD11c+ cells. As expected, two vaccinations at birth and day 7 had a significant effect on CD11c+ cells. The various effects are shown in FIG. 2.

Second set of experiments: One-week-old mice that were vaccinated at birth with $2.5 \times 10^7$ TCID$_{50}$ of MVA-BN showed a different composition of immunologically relevant cell populations in spleen and blood than control mice (Table 1). In blood there was an increase in the CD8 positive lymphocyte population as well as an increase in the number of NK cells. The number of CD11c positive cells was about 3 times higher than in controls and the percent of B-cells (B220 and CD19 double positive cells) was significantly decreased. In the spleen the total number of cells did not differ between immunised animals and controls. In contrast to the blood, the spleen of vaccinated animals had more CD4 positive T lymphocytes than controls and the number of NK cells was not increased. Similar to blood the relative number of CD8 positive lymphocytes were increased and the number of B-cells decreased. The percentage of CD11c positive cells was about 3 times higher than in controls. We first recognised a difference in the percentage of dendritic cells at day 5 following vaccination with MVA-BN, when the number of CD11c positive cells in the spleen of 4 untreated controls were 3.6%, compared to 4.8% in 4 MVA-BN vaccinated mice. The same amount of UV-inactivated MVA-BN did not cause any significant change in the cell populations after vaccination of neonatal mice compared to controls (data not shown). The initial vaccination dose was chosen arbitrarily. After titration of the inoculum we selected a standard dose of $2.5 \times 10^6$ TCID$_{50}$ for vaccination (10 time less than in the initial experiment). At this dose maximal numbers of DC were induced (Table 2).

TABLE 1

Changes induced in blood and spleen cells in newborn mice 1 week after immunisation with $2.5 \times 10^7$ TCID$_{50}$ MVA-BN

| | Blood | | | Spleen | | |
|---|---|---|---|---|---|---|
| Parameter % | NaCl | MVA-BN | P* | NaCl | MVA-BN | P* |
| Total cells × $10^6$ | | | | 17.9 ± 1.9 | 24.1 ± 2.6 | 0.105 |
| % CD11c | 5.4 ± 1.3 | 18.6 ± 1.5 | 0.001 | 2.8 ± 0.1 | 7.9 ± 0.8 | 0.001 |
| % CD11c/CD8α | 0.5 ± 0.1 | 2.7 ± 0.3 | 0.001 | 1.1 ± 0.1 | 4.6 ± 0.7 | 0.002 |
| % CD4/CD3 | 16.9 ± 1.1 | 16.1 ± 1.5 | 0.999 | 4.8 ± 0.3 | 8.1 ± 1.5 | 0.004 |
| % CD8α/CD3 | 6.0 ± 0.9 | 10.3 ± 0.9 | 0.002 | 4.7 ± 0.3 | 8.4 ± 1.1 | 0.002 |
| % NK1.1/DX5 | 16.4 ± 1.2 | 24.4 ± 3.3 | 0.032 | 2.5 ± 0.3 | 2.4 ± 0.2 | 0.862 |
| % CD19/B220 | 22.3 ± 0.5 | 8.4 ± 0.8 | 0.001 | 16.2 ± 1.3 | 8.6 ± 0.9 | 0.004 |

*Mann-Whitney U-Test

TABLE 2

Induction of CD11c positive cells in the spleen of 1-ay-old wt mice and mice with gene-targeted disruptions within 7 days after MVA-treatment.

| Mouse strain | MVA dose (TCID$_{50}$) | controls % CD11c | MVA-BN % CD11c | ratio |
|---|---|---|---|---|
| wt[a] | $2.5 \times 10^7$ | 2.8 | 7.9 | 2.8 |
| wt | $2.5 \times 10^6$ | 2.1 | 11.9 | 5.6 |
| wt | $2.5 \times 10^5$ | 2.5 | 6.6 | 2.6 |
| RAG[b] | $2.5 \times 10^7$ | 4.2 | 5.4 | 1.3 |
| AG129[c] | $2.5 \times 10^3$ | 2.6 | 2.7 | 1.0 |

[a] Wt = either C57BL/6 or 129 Sv/Ev mice.
[b] RAG mice deletion in recombination activating gene (i.e no functional T and B cells).
[c] AG129 gene targeted disruptions of IFN receptor Type I (IFN-α and -β) and Type II (IFN-γ)

(ii) MVA-BN Induces Preferentially Plasmacytoid Dendritic Cells (pDC)

According to other authors CD11c positive cells that also expressed CD45RA or CD45R were considered as pDC (Asselin-Paturel, et al. 2001, *Nat Immunol*, 12: 1144). It was asked whether MVA-BN induced an increase of pDC. A further experiment was performed in which also CD45RA or CD45R on CD11c positive were analysed. The percentage of CD11c and CD45R double positive cells was significantly higher in MVA-BN treated mice (5.6±0.7%) than in both control groups (untreated 3.0±0.3%, p=0.01; UV-inactivated MVA-BN 3.0±0.2%, p=0.006. Mann-Whitney U-test).

(iii) Neonatal Mice Treated with MVA-BN have Elevated Levels of Serum Flt3-L

Flt3-L is a hematopoetic factor that leads to increased levels of DC in adult animals. In human and possibly mice the richest source of this factor are activated T cells. To determine whether the elevated numbers of DC could be the results of induced Flt3-L, serum of MVA-BN treated mice was compared to mock treated animals for the presence of this factor. Animals treated at day 2 and 5 had twice the levels of Flt3-L in the serum when compared to serum of mock treated animals. Hence, Flt3-L is one of the factors that could be made responsible for elevated numbers of DC (FIG. 3)

The time course of the Flt3-L induction in newborn mice was assessed after administration of MVA-BN. In newborns, MVA-BN vaccination induced an increase in Flt3-L concentration within 24 hours. The induction reached a maximum after 48 hours and was still present at day 7, the time when spleen cells were usually analyzed and resistance against HSV-1 was tested (see below). In the vaccinated mice the Flt3-L concentration in the serum was two-fold increased 24 hours and 48 hours after the vaccination, compared with age matched control animals.

Example 2

(i) MVA-BN Treated Neonatal Mice Survive a Challenge with 100 to 500 $LD_{50}$ of HSV-1

Groups of mice were treated with the standard dose of MVA-BN one or 2 days after birth and challenged at 7-8 days of age with 100 to 500 $LD_{50}$ of Herpes simplex virus 1 (HSV-1) (FIG. 4). MVA BN treated mice survived the challenge with HSV 1, whereas all the control mice died within 5-6 days after inoculating the challenge virus.

To further support these observations, 9 challenge experiments were performed with 40 MVA BN treated and 45 control mice. More than 80% of the virus treated mice survived the challenge, whereas all the control mice died (FIG. 5).

In a separate set of experiments the mice were treated at birth with MVA-BN ($2.5 \times 10^6$ $TCID_{50}$/mouse). At day 8 a challenge with either $10^3$ (1 $LD_{50}$) or $10^5$ (100 $LD_{50}$) PFU of HSV-1 was performed. Following MVA-BN vaccination 65% of the mice survived a viral dose that killed 100% of the control mice (100 $LD_{50}$) and 90% survived a dose that killed 45.5% of the controls (1 $LD_{50}$). In additional experiments a group of 7 mice vaccinated with UV-inactivated MVA-BN were infected with HSV-1. Five of them died within 7 days. The remaining 2 animals ceased to grow and died at day 22 and 29. Therefore, mice treated with MVA-BN reached a state of increased resistance against HSV-1 that was associated with live MVA-BN, but not inactivated MVA-BN.

In control experiments done with mice that do not have functional T-cells it was determined that the protection against HSV-1 after vaccination with MVA-BN was not due to cross-reacting cytotoxic T-lymphocytes induced by MVA-BN.

It was tested whether DC cells were responsible for the protection of mice from HSV-1 after vaccination with MVA-BN. To this end naive 8-day-old mice were challenged with $5 \times 10^4$ PFU HSV-1 4 hr after transfer of cells from MVA-treated mice. In a first experiment splenocytes from 8-days-old mice treated at 1 day of life with MVA-BN were separated in DC rich (low-density) and DC poor (high-density) fractions. Mice receiving $5 \times 10^6$ cells from the DC rich fraction survived the challenge to 50% whereas all the mice receiving 10 times less DC rich suspension or untreated mice died within 5 days. A second approach was done by transferring positively isolated CD11c positive cells from 8-days-old mice treated at 1 day of life with MVA-BN to naive age matched mice. A suspension of $2 \times 10^6$ splenocytes containing more than 80% CD11c positive cells from MVA-BN treated mice protected naive mice from HSV-1 infection. In contrast, 4 untreated littermates as well as 8 additional untreated animals died after the challenge. Furthermore, mice receiving the same amount of spleen cells or mice receiving one spleen equivalent ($50 \times 10^6$ cells) from the negative fraction did not show increased resistance against HSV-1. Thus CD11c positive cells are able to protect mice from HSV-1.

After administration of MVA short-term protective effects in the range of about 24 hours were described in the prior art (Vilsmeier, B., Berl. Münch. Tierärztl. Wschr. 112 (1999), 329-333). Although the viruses used in said publication are not viruses that are not capable of being replicated to infectious progeny virus in the neonatal or prenatal animal used, it was tested whether the mode of action as disclosed in Vilsmeier is similar to the mode of action described in the present application. More particularly, Vilsmeier discloses that MVA, in particular inactivated MVA, induces a paramunity for about 24 hours. To test whether the paramunity effect counts also for the protective effects as disclosed in the present application mice 24 hours of birth were vaccinated either with MVA-BN or with inactivated MVA-BN. At 7 days of age the mice were challenged with a lethal dose of HSV-1 ($10^5$PFU HSF-1f). Unvaccinated control mice died 6 days after challenge. Also the mice vaccinated with inactivated MVA-BN were not protected against a challenge with HSV-1. The number of DC cells in these mice was not elevated. In contrast, the mice vaccinated with non-inactivated MVA-BN were significantly protected against a challenge with HSV-1. 30 days after the challenge more than 80% of the mice were still alive. Two days after vaccination elevated serum Flt3-L was found in the serum. Elevated numbers of DC were found in the spleen. The enhanced Flt3-L was associated with elevated numbers of DC. This confirms that paramunity effects are not responsible for the observed protection.

(ii) MVA-BN Induces a Specific Immunity in Neonates that Lasts Until Adulthood

One-day-old C57Bl/6 mice (group size of 18) were vaccinated (i.p) with MVA-BN ($2.5 \times 10^7$ $TCID_{50}$). Four weeks after vaccination, when the mice were considered adults there where challenged with a lethal dose ($1 \times 10^4$ $TCID_{50}$) of vaccinia Western Reserve (VV-WR). With the exception of one animal all other MVA-BN vaccinated animals survived. In contrast, all placebo vaccinated animals died within 7 days and demonstrated severe clinical symptoms such as ruffled fur, weight loss and reduced activity. Clearly this is a clear demonstration that MVA-BN vaccination is not only safe in neonatal animals, but is capable of inducing a protective immune response against a lethal vaccinia (related virus to MVA-BN) infection.

The invention claimed is:

1. A method for inducing an immune response in an immune-compromised animal comprising administering to the immune-compromised animal an MVA virus characterized by being capable of reproductive replication in vitro in chicken embryo fibroblasts and by being non-replicative in vitro in the human keratinocyte cell line HaCaT and the human cervix adenoma cell line HeLa, wherein the administration of the MVA virus increases the number of dendritic cells or their precursors in the animal.

2. The method of claim 1, wherein the animal is a human.

3. The method of claim 2, wherein the MVA virus is non-replicative in vitro in the human keratinocyte cell line HaCaT, the human embryo kidney cell line 293, the human bone osteosarcoma cell line 143B, and the human cervix adenoma cell line HeLa.

4. The method of claim 2, wherein the MVA virus is MVA-BN as deposited at the ECACC with the deposition number V000083008.

5. The method of claim 2, wherein the human is infected with a human immunodeficiency virus.

6. The method of claim 5, wherein the human immunodeficiency virus is HIV-1.

7. The method of claim 5, wherein the human immunodeficiency virus is HIV-2.

8. The method of claim 2, wherein administration of the MVA virus increases the number of T-lymphocytes in the animal.

9. The method of claim 2, wherein the administration of the MVA virus increases the level of Flt3-L in the animal.

10. The method of claim 2, wherein the MVA virus is a recombinant virus.

11. The method of claim 2, wherein the MVA virus is administered by oral, nasal, intramuscular, intravenous, intraperitoneal, intradermal, intra-utero, or subcutaneous application.

12. The method of claim 2, wherein the animal has a level of CD4+ cells in the blood of less than 400/µl.

* * * * *

UNITED STATES PATENT AND TRADEMARK OFFICE
CERTIFICATE OF CORRECTION

| | |
|---|---|
| PATENT NO. | : 7,897,156 B2 |
| APPLICATION NO. | : 12/118841 |
| DATED | : March 1, 2011 |
| INVENTOR(S) | : Ackermann et al. |

It is certified that error appears in the above-identified patent and that said Letters Patent is hereby corrected as shown below:

Title page, Item (63) should read:

"Continuation-in-part of application No. 11/341,955, filed on Jan. 27, 2006, now abandoned, which is a continuation-in-part of application No. 10/418,854, filed on Apr. 18, 2003, now U.S. Pat No. 7,097,842, which is a continuation-in-part of application No. PCT/EP01/13628, filed on Nov. 22, 2001."

Col. 1, line 9, replace "Nov. 11, 2001" with --Nov. 22, 2001--.

Col. 21, line 8, replace "adenoma" with --adenocarcinoma--.

Col. 21, line 16, replace "adenoma" with --adenocarcinoma--.

Signed and Sealed this
Third Day of May, 2011

David J. Kappos
*Director of the United States Patent and Trademark Office*